US012016283B2

(12) United States Patent
Beem et al.

(10) Patent No.: US 12,016,283 B2
(45) Date of Patent: *Jun. 25, 2024

(54) COMPOSITIONS AND THEIR USE FOR PEST CONTROL AND TO INDUCE PLANT HORMONE AND GENE REGULATION FOR IMPROVED PLANT PRODUCTION AND DEFENSE

(71) Applicant: Biodel AG Inc., Maricopa, AZ (US)

(72) Inventors: Lance William Beem, Maricopa, AZ (US); Stephen Michael Butler, Maricopa, AZ (US); George Benjamin Cloud, Chandler, AZ (US)

(73) Assignee: BIODEL AG INC., Maricopa, AZ (US)

( * ) Notice: Subject to any disclaimer, the term of this patent is extended or adjusted under 35 U.S.C. 154(b) by 226 days.

This patent is subject to a terminal disclaimer.

(21) Appl. No.: 17/375,363

(22) Filed: Jul. 14, 2021

(65) Prior Publication Data

US 2021/0337751 A1 Nov. 4, 2021

Related U.S. Application Data

(63) Continuation of application No. 16/707,149, filed on Dec. 9, 2019, now Pat. No. 11,083,147, and a continuation of application No. 16/707,136, filed on Dec. 9, 2019, now Pat. No. 11,076,543, which is a continuation of application No. 15/518,414, filed as application No. PCT/US2016/046378 on Aug. 10, 2016, now Pat. No. 10,542,686.

(60) Provisional application No. 62/202,998, filed on Aug. 10, 2015.

(51) Int. Cl.
*A01H 3/04* (2006.01)
*A01N 65/12* (2009.01)

(52) U.S. Cl.
CPC .............. *A01H 3/04* (2013.01); *A01N 65/12* (2013.01)

(58) Field of Classification Search
CPC .................................. A01H 3/04; A01N 65/12
See application file for complete search history.

(56) References Cited

U.S. PATENT DOCUMENTS

| 2,393,035 | A | 1/1946 | Edwards et al. |
| 4,988,388 | A | 1/1991 | Scholman, Jr. |
| 5,532,298 | A | 7/1996 | Monroe et al. |
| 2002/0006987 | A1 | 1/2002 | Nakayama et al. |
| 2006/0149015 | A1 | 7/2006 | Cornish et al. |
| 2010/0160160 | A1* | 6/2010 | Hewlett ............ A01G 22/05 504/100 |
| 2010/0235950 | A1 | 9/2010 | Pennell |
| 2013/0142759 | A1* | 6/2013 | Reed ................. A01N 63/22 424/93.46 |
| 2015/0125435 | A1* | 5/2015 | Yamashita ......... A01N 25/30 424/93.51 |
| 2015/0136882 | A1 | 5/2015 | Huang et al. |

FOREIGN PATENT DOCUMENTS

| CA | 2325372 A1 | 9/1999 |
| CN | 103175932 A | 6/2013 |
| EP | 0227806 B1 | 8/1989 |
| WO | 2014127206 A2 | 8/2014 |

OTHER PUBLICATIONS

B. Lapornik et al., "Comparison of extracts prepared from plant by-products using different solvents and extraction time," Journal of Food Engineering 71 (2005) 214-222.*
"Betaine Hydrochloride," <https://www.rxlist.com/betaine_hydrochloride/supplements.htm>. published Nov. 26, 2012, pp. 1.
"Mesh to Micron Conversion Chart," <https://www.skylighter.com/blogs/fireworks-information/mesh-to-micron-conversion-chart>, published Feb. 14, 2018, pp. 1-2.
"Pebble Mill Grinding," <https://www.911metallurgist.com/blog/pebble-mills>, Copyright 2012*2017, 911 Metallurgist, pp. 1-6.
Bultman, J.D., et al., "Anti-termitic efficacy of the resin and rubber in fractionator overheads from a guayule extraction process." Industrial Crops and Products, 1998, 8: 133-143.
Cespedes, C. et al., "Insect Growth Regulatory Activity of Some Extracts and Compounds from Parthenium argentatum on Fall Armyworm *Spodoptera frugiperda*." Z. Naturforsch., Aug.-Oct. 2000, 56(1-2):95-105.
Lapornik, B., et al., "Comparison of Extracts from Plant by-products Using Different Solvents and Extraction Time." Journal of Food Engineering, 2005, 71(2): 214-222.
Murray, C.W., et al., "Isolation of Betaine from Guayule." Journal of the American Chemical Society, 1945, 67(2): 1422.
Nakayama, F.S., "Guayule Future Development." Industrial Crops and Products, 2005, 22:3-13, doi: 10.1016/j.indcrop.2004.05.006.
Schloman, W.W. Jr., et al., "Guayule Byproduct Evaluation: Extract Characterization." J. Agric. Food Chem., 1983, 31: 873-876.
War, A.R. et al., "Mechanisms of Plant Defense Against Insect Herbivores." Plant Signaling & Behavior, Aug. 2012, 7(1):1306-1320, doi: 10.4161/psb.21663.
Zafari, M. et al., "Effect of Plant Hormone Auxin in Flower Development." Agri. Sci. Dev., Feb. 2015, 4(2):27-30.

(Continued)

*Primary Examiner* — Monica A Shin
(74) *Attorney, Agent, or Firm* — SALIWANCHIK, LLOYD & EISENSCHENK

(57) ABSTRACT

The subject invention provides compositions and methods of using the same for improving plants' defense by employing naturally-derived chemicals. In a specific embodiment, the composition is from *Parthenium argentatum* Gray, also known as the guayule plant. Preferred compositions can up- or downregulate growth genes responsible for the targeted plants' defense mechanisms in order to create physical and/or chemical barriers, and produce detouring exudates, antagonistic compounds, or fumigating compounds that prevent and treat damages from pests in agronomic or non-agronomic plants.

8 Claims, 16 Drawing Sheets

(56) References Cited

OTHER PUBLICATIONS

Beauvieux, R., et al., "Bud Dormancy in Perennial Fruit Tree Species: A Pivotal Role for Oxidative Cues." Frontiers in Plant Science, May 2018, 9(657): 1-13.

Fadon, E., et al., "A Conceptual Framework for Winter Dormancy in Deciduous Trees." Agronomy, 2020, 10(241):1-20.

Maged, S.M., et al., "Effect of Some Dormancy Breaking Agents on Flowering and Fruiting of Le-Conte Pear Trees under Giza Conditions." Journal of Horticultural Science & Ornamental Plants, 2019, 11(3): 222-231.

* cited by examiner

Means followed by same letter do not significantly differ (P=.05, Duncan's New MRT)

COMPOSITIONS AND THEIR USE FOR PEST CONTROL AND TO INDUCE PLANT HORMONE AND GENE REGULATION FOR IMPROVED PLANT PRODUCTION AND DEFENSE

CROSS-REFERENCE TO A RELATED APPLICATION

This application is a continuation application of co-pending U.S. application Ser. No. 16/707,149, filed Dec. 9, 2019; and U.S. application Ser. No. 16/707,136, filed Dec. 9, 2019; which is a continuation application of U.S. application Ser. No. 15/518,414, filed Apr. 11, 2017, now U.S. Pat. No. 10,542,686; which is a National Stage Application of International Application No. PCT/US2016/046378, filed Aug. 10, 2016; which claims the benefit of U.S. provisional application Ser. No. 62/202,998, filed Aug. 10, 2015, all of which are incorporated herein by reference in their entirety.

BACKGROUND OF THE INVENTION

The market for treating cyst nematodes in sugar beets, cole crops, and particularly soybeans is very large. As synthetic contact nematicide chemistry and soil fumigants face greater scrutiny, and as new nematicide, insecticide, bactericide, and fungicide chemistry pipelines shrink due to increasing regulatory thresholds, sustainable biological pesticides such as plant extracts are becoming more important alternatives, particularly those that give similar levels of control as the conventional pesticides and fumigants. Economic and environmental conditions create opportunities for biological treatments of diseases caused by plant parasitic nematodes, insects, mites, bacteria, and fungi. As a result, there is a significant demand for more environmentally-friendly solutions that makes the investment in research and development of new biologically derived nematicides worthwhile.

Currently, $1.5 billion a year is lost to soybean cyst nematode alone. Resistant soybean varieties do not last long because of the difficult crosses for hybrids with resistance. The genetic pool is diverse and breaks resistance in 2 to 3 years on average. Applications other than seed treatments in the past have been expensive. Therefore, applying contact nematicides placed in the seed furrow at planting has been the primary application method. Because of toxicity toward animals nearby, such as birds, overhead center pivots with liquid applications of toxic compounds such as Nemacur, Temik, Furadan, Dazinat and Mocap have all fallen out of favor.

Methyl bromide, a synthetic soil fumigant, poses health and environmental hazards, and is being phased out under an international ban. Since the 1960's, methyl bromide has been used by growers to effectively sterilize fields before planting to primarily control nematodes, as well as to treat disease and weeds; however, because this toxic compound is used in gas form, more than half the amount injected into soil can eventually end up in the mr. Rising into the atmosphere, it contributes to the thinning of the ozone layer. In 2005, developed countries banned methyl bromide under the Montreal Protocol, which is an international treaty signed in 1987 to protect the stratospheric ozone layer.

Under the ban, the treaty allows limited use of methyl bromide In strawberries, almonds, and other crops that lack alternatives for both effective and affordable control of nematodes, disease, and weeds. The extent of authorized use diminishes every year and will likely end soon. Finding alternatives to methyl bromide is, thus, a priority to the USDA, which provided a $5 million grant that supported research to identify alternatives since 2010. However, no single product provides the wide spectrum of control offered by methyl bromides. Growers facing the inevitable transition to alternative products are seeking viable alternatives with varying degrees of success.

Historically, "soft" nematicides, such as those derived from bacteria or fungi, have been used. They are generally weaker and can rapidly leach through the soil, lacking the residual effect to control the nematodes. The biologically derived cinnamic acid, on the other hand, offers potent initial control, short-duration residual control, and the safety of soft nematicides. As an example, the guayule plant, also known as *Parthenium argentatum* Gray, is currently being grown commercially in limited quantities for the extraction of latex rubber. The concentration of cinnamic acid in the resin fraction of the guayule plant has been well known due to prior commercialization attempts for rubber extraction in the 1940's and the 1980's. However, what has not been well know until this recent discovery is the effect of various compounds and the derivatives thereof harvested from the guayule plant in treating and controlling nematodes and other plant pests has not been extensively studied. Although the guayule has been known to be resistant to endoparasitic nematodes such as root knot and lesion nematode since 1948, the assumption was that cinnamic acid exudates were the reason for reduction or non-entry of these endoparasites into the root. However, in accordance with the current invention it has been found that enzymes and plant hormones in a guayule extract are also greatly involved with multiple modes of action to control or suppress plant parasitic nematodes, insects and increase plant productivity through upregulation of plant genes.

BRIEF SUMMARY OF THE INVENTION

The subject invention provides compositions and methods for improving plants' defense against exogenous attacks by employing one or more compounds extracted from a single or multiple species of plants. The subject invention further provides materials and methods useful for gene and plant growth regulation.

In a specific embodiment, the composition comprises one or more isoprenoid and other compounds, derived from *Parthenium argentatum* Gray and more specifically, trans-cinnamic acid; 3,4-dihydroxyhydrocinnamic acid; and 3-hydropropionic acid. These compounds can be used along with enzymes that, when applied to nematodes or insects, can, for example, dissolve chitin and/or protein of molting insects. The enzymes may be, for example, latex/rubber transferases.

Compositions provided herein can be used to treat living plants and plant-derived products such as dried wood, dried roots, lumber, and dried fruits.

Preferred compositions can regulate expression of genes responsible for the plants' defense mechanisms in order to create physical and/or chemical barriers, and/or induce the plant to produce detouring exudates, antagonistic compounds, and/or fumigating compounds that prevent and/or treat damage from pests in agronomic or non-agronomic plants.

Thus, in one aspect, the subject invention provides a composition for regulating a target plant's genes and/or hormones such as, for example, plant growth regulators (PGRs), wherein the composition comprises one or more compounds that can be extracted from parts of plants, or a derivative of such a compound.

In specific embodiments, the compounds are from plants that are grown in harsh environments, such as, for example, dry environments, highly salinity environments, high altitude, extreme pH and/or extreme temperature. Advantageously, when applied at proper rates, in certain embodiments, compositions provided herein are used to repel, resist, remove, disable, fumigate, alter, and/or kill pests in a variety of environments.

The compounds may have, for example, at least one of the following effects: increasing a plant's repellency through exudates, inducing a plant's systemic resistance against exogenous attacks, and enhancing a plant's physical and chemical barriers. In certain preferred embodiments, the compositions comprise isoprenoid compounds.

In certain embodiments, the compound can be cinnamic acid, or a derivative thereof. The compound can also be a protease or chitinase. Preferably, the compounds are extracted from a desert plant *Parthenium argentatum* Gray, also referred to as the guayule plant.

In some embodiments, the composition further comprises one or more additives that can be selected from, for example, wetting agents, adjuvants, and inert chemicals.

Exemplary embodiments provide compositions that comprise isoprenoids that can up or down-regulate one or more genes that are directly or indirectly involved in a plant's defense system, including secondary metabolites found in a plant's defense-building pathways. In preferred embodiments, the effects of the genetic and/or hormonal regulations are temporary without permanently modifying the plant's genes.

In certain embodiments, the exogenous attacks can be biotic or abiotic in nature. Non-limiting examples of biotic attacks include plant parasites, herbivores, bacteria, fungi, and invasive plants such as weeds. Abiotic attacks can be caused by, for example, changes in the plant's environment. In some embodiments, the exogenous attacks are abiotic in nature, originating from extreme physical conditions that include, but are not limited to, changes in temperature, light exposure, salinity, water quality, soil, and other factors affecting the target plant's growth.

In a specific embodiment, the compositions provided herein are effective in treating plants infested with parasitic nematodes. In one embodiment, the population of beneficial microbes is maintained or enhanced.

In another aspect, the subject invention provides a method of improving a target plant's defense against exogenous attacks, comprising temporarily regulating the plant's genes and/or hormones by externally applying, either on or near the plant, a composition of the subject invention. The genetic and/or hormonal regulations may have one or more of the following effects: increasing the plant's repellency through exudates, inducing the plant's systemic resistance against the attacks, and enhancing the plant's physical and/or chemical barriers.

In some embodiments, the chemical barriers resulting from the genetic regulations provided herein include, but are not limited to, production of antagonistic compounds such as phytoalexins, fumigating compounds, and compounds that can alter the taste, smell, and/or pheromones characteristic to the target plant.

In certain embodiments, the genetic and/or hormonal regulations are effective in inhibiting the pests' abilities to find, penetrate, and subsequently consume the target plant. Further, in certain embodiments, the compositions of the subject invention can interfere with the pests' ability to mate.

In some embodiments, the composition is applied as a seed treatment or to the soil surface with or without mechanical incorporation.

Advantageously, preferred embodiments of the subject invention provide naturally-derived treatments without permanently modifying the plants' genes, and are effective in improving crop yield and maintaining the health of the soil. Further, unlike conventional pesticides that only kill pests, in certain embodiments compositions provided herein can improve a target plant's own defense mechanisms against exogenous attacks.

Objects, features, and advantages of the invention will be apparent to those skilled in the art from the detailed description of the invention which will now follow, taken in conjunction with the tables, drawings, and the accompanying claims.

DETAILED DESCRIPTION OF THE INVENTION

Figure 1:
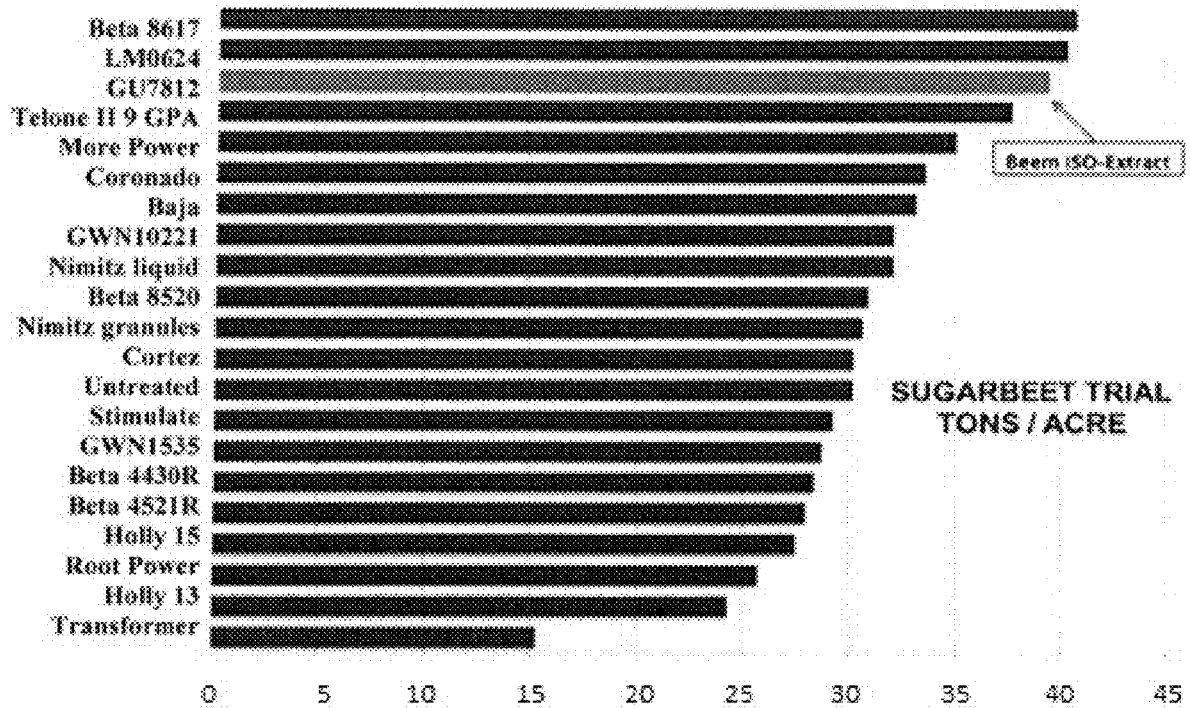
FIG. 1 shows increased sugarbeet yield.

The subject invention provides compositions and methods for improving a plant's defense against attacks and/or modulating plant growth and/or health. Specifically exemplified herein are compositions comprising naturally-derived compounds that can be extracted from plants, or derivatives of such compounds. In a specific embodiment, the compositions of the subject invention comprise an isoprenoid compound, and more specifically, trans-cinnamic acid, or derivatives thereof, extracted from *Parthenium argentatum* Gray.

Compositions provided herein can be used to treat living plants as well as plant derived products such as dried wood, dried roots, lumber, and dried fruits. Preferred compositions can regulate expressions of genes responsible for the plant defense and/or growth and/or health. In certain embodiments, the compositions of the subject invention can be used to induce the plant to create physical and/or chemical barriers so as, for example, producing detouring exudates, antagonistic compounds, or fumigating compounds that prevent, reduce and/or repair damage from pests and/or physical insults in agronomic and/or non-agronomic plants.

Advantageously, preferred embodiments of the subject invention provide naturally-derived treatments that can be used to achieve the advantageous results without permanently modifying a plant's genes. Advantageously, in certain embodiments, the compositions and methods are effective in improving crop yield and maintaining the health of the soil.

In one aspect, the subject invention provides compositions for regulating a target plant's genes and/or hormone production such as, for example, plant growth regulators (PGRs). In preferred embodiments, the compositions of the subject invention comprise compounds that can be extracted from plants that grow in harsh environments, or derivatives of such compounds. In preferred embodiments, the composition has one or more of the following effects: increasing a plant's ability to repel one or more pests via exudates, inducing the plant's systemically acquired resistance against exogenous attacks, and enhancing the plant's physical and chemical barriers. In certain embodiments, the composition comprises an isoprenoid compound.

An isoprenoid compound, as used herein, comprises two or more isoprene molecules bonded together as the backbone structure with optionally substituted functional groups attached thereto. An unsubstituted isoprene molecule, also known as 2-methy-1,3-butadiene, is an unsaturated hydrocarbon molecule. Cinnamic acid and its hydroxy derivative caffeic acid, 3,4-dihydroxyhydrocinnamic acid and 3-hydropropionic acid. The subject invention also contemplates the use of latex/rubber transferase enzymes.

In some embodiments, the isoprene molecules can be extracted from a plant such as, but not limited to, *Selaginella lepidophylla*, *Parthenium incanum*, *Parthenium argentatum* Gray, *Yucca schidigera*, *Quillaja saponaria*, *Betula species*, *Juglans* species, and/or *Ascophyllum* species.

In some embodiments the plant is one that grows in a harsh environment. The harsh environment can be, for example, one that lacks necessary precipitation for growing other plants, areas located at elevated altitude, areas having high salinity, and areas characterized by extreme temperatures or pH of the soil. Non-limiting examples of harsh environments include deserts and other arid regions, mountains, and land near bodies of saltwater such as oceans or saltwater lakes.

In certain embodiments, arid conditions refer to a location that receives less than 15, 10, 5, or 2 inches of rain per year. In certain embodiments, elevated altitude refers to higher than 5,000; 7,000; 9,000; or 11,000 feet above sea level. In certain embodiments, high salinity refers to a salinity in the growing medium (e.g., soil) as measured by electrical conductivity of greater than 3.5 mmhos/cm, 4.0 mmhos/cm, or 4.5 mmhos/cm. In certain embodiments, extreme temperatures refer to below 0° C., −5° C., −15° C., or −20° C. In certain embodiments, extreme temperatures refer to above 30° C., 35° C., 40° C., or 45° C. In certain embodiments, extreme pH refers to below 5, 4, or 3, or above 9, 10, or 11.

In a specific embodiment, the isoprenoid compound preferably comprises cinnamic acid in the trans form, or derivatives thereof, extracted from *Parthenium argentatum* Gray, the guayule plant, typically grown in desert environments. Non-limiting examples of derivatives of cinnamic acid are caffeic acid; 3,4-dihydroxyhydrocinnamic acid; and 3-hydropropionic acid.

In some embodiments, the compounds useful according to the subject invention can be extracted from a whole plant or from a part of the plant. Non-limiting examples of these plant parts include seed, pollen, wax, stems, leaves, fruit, reproductive parts, roots, and trichomes. In a specific embodiment, the compositions are derived from the roots of the plant. Advantageously, the compositions of the subject invention, which can be derived from these plants or plant parts, can be used to promote plant health and/or growth according to the subject invention without adversely impacting the environment to which they are applied. In addition, these compositions are non-toxic to humans, birds, fish, livestock and pets.

In some embodiments, the compositions can be extracted using an aqueous extraction procedure. Embodiments of the subject invention also provide methods of extracting and packaging the compositions.

Advantageously, in certain embodiments the subject invention provides compositions with trans-cinnamic acid, 3,4-dihydroxyhydrocinnamic acid, derived from natural plant sources rather than from synthetic methods yielding cinnamic aldehydes, which are found in conventional products. The chemical procedures involving saponin skeleton and terpene are safe and effective for use in agronomic and minor crops, greenhouses, golf courses, turf farms, outdoor nurseries, hydroponics, and outdoor plants in neighborhoods, without causing concerns for toxicity to humans, birds, and other plant and/or animal life in proximity to the site of treatment.

In some embodiments, the composition further comprises additives selected from, for example, wetting agents, adjuvants, and inert chemicals.

Evidence from trials has confirmed the effectiveness of using a guayule-derived composition as the primary active ingredient optionally blended with other biological compounds in controlling parasitic nematodes and other pests. Biological compounds suitable for blending with guayule extract include, for example, saponins derived from *quillaia*, which is itself an extract of *Quillaja saponaria*, commonly known as the soap bark tree, and extracts of the desert plant *Yucca schidigera*. Saponins can also serve as a surfactant for the blended composition.

In preferred embodiments, the effects of the genetic and/or hormonal regulations are temporary without permanently modifying a plant's genes. Therefore, unlike genetically modified organisms (GMOs), external application of the composition can be used to achieve a targeted and controlled effect.

In an exemplary embodiment, using an aqueous extraction of molecules from the whole plant or the roots of a guayule plant, it is determined that the residual for cyst nematodes can to be approximately two weeks before repeating the application.

Unlike root knot nematodes, half the population (the males) of cyst nematodes are of the root system for the first month of the nematode life cycle. As a result, when applied properly the residual of the compositions provided herein can be effective at an early stage before they dissipate.

In specific embodiments, the compositions of the subject invention can be used to modulate the expression of genes that are directly or indirectly involved in the functions of plant growth regulators (PGRs), as well as secondary metabolites such as, for example, flavoids, found in the plant's defense-building pathways. Three primary components of the Guayule plant extract are aspartic acid, which conjugates auxin when applied to the upper part of the plants tested, as well as impact roots when treated, as well as succinic and lactic acid, which act on the root system to increase lateral root growth. In preferred embodiments, the subject composition further comprises aspartic acid, cysteine, and glutamine.

Five principal categories of plant hormones are: auxins, cytokinins, gibberellins, abscisic acid, and ethylene. One additional category of plant hormones is jasmonates, of which jasmonic acid is a non-limiting example. Auxins, primarily indole-3-acetic acid (IAA), promote both cell division and cell elongation, and maintain apical dominance. Auxins also stimulate secondary growth in the vascular cambium, induce the formation of adventitious roots and promote fruit growth.

In some embodiments of the current invention, genes regulating all categories of the aforementioned plant hormones respond to the treatment comprising the compositions of the subject invention.

A non-exhaustive list of the genes that can be up or down regulated includes GA-biosynthetic GA1 (cds) (Acc. No. AT4G02780), GA2 (eks) (Acc. No. AT1G79460), AtKO1lGA3 (Acc. No. AT5G25900), CYP88A3/KAO2 (Ace. No. ATIG05160), AtGa20ox/Ga5 (Ace. No. AT4G25420), AtOX3 (Ace. No. ATI G 15550), At20X (Ace. No. ATI G02400), ABA-biosynthetic PDS (Ace. No. AT5GI7230), ZEP (Ace. No. AT5G67030), (NCED #I) (Ace. No. AT4GI8350), NCED #2 (Ace. No. ATI G78390), NCED3 cplast (Ace. No. AT3G 14440), (NCED #4) (Ace. No. AT3G24220), NCED5 cplast (Ace. No. ATIG30100), SDR,ABA2/GINI (Ace. No. ATIG52340), AA03 (Ace. No. AT2G27150), MOCO,LOS5/ABA3 (Ace. No. AY034895), ABA 8' hydroxylase IAA-biosynthetic/related (Ace. No. CYP707 A4), cyp mono oxygenase (Ace. No. AT4G39950), cyp monooxygenase (Ace. No. AT2G22330), TRP monooxygenase (Ace. No. AT4G32540), nitrilase (Ace. No. AT3G44300), nitrilase (Ace. No. AT3G44310), nitrilase (Ace. No. AT3G44320), hydrolase/nitrilase (Ace. No. AT4G08790), aldehyde oxidase (Ace. No. AT5G20960), IAA deconjugation (Ace. No. AT5G56660), IAA deconjugation (Ace. No. ATIG51760), IAA deconjugation (Ace. No. AT3G02875), IAA conjugation (Ace. No. AT2G23260), IAA receptor (Ace. No. AT3G62980), IAA influx carrier (Ace. No. AT2G38120), IAA efflux carrier (Ace. No. ATIG73590), Auxin redirection at root tip ETH-biosynthetic (Ace. No. AT2G47000), ACC oxidase (Ace. No. ATIG05010), ACC oxidase (Ace. No. ATIG62380), ACC synthase (Ace. No. AT2G22810), ACC synthase (Ace. No. AT5G65800), ACC synthase (Ace. No. AT4G11280), ACC synthase (Ace. No. AT4G37770), ACC synthase (Ace. No. AT4G08040), CYK-biosynthetic CYK synthase (Ace. No. ATIG25410), CYK synthase (Ace. No. AT3GI9160), CYK Synthase (Ace. No. AT3G63110), CYK synthase (Ace. No. AT4G24650), CYK synthase (Ace. No. AT5G 19040), CYK oxidase (Ace. No. ATI G75450), CYK oxidase (Ace. No. AT2GI9500), CYK oxidase (Ace. No. AT2G41510), CYK oxidase (Ace. No. AT3G63440), CYK oxidase (Ace. No. AT4G29740), CYK oxidase (Ace. No. AT5G21482), CYK oxidase (Ace. No. AT5G56970), and PDF1.2c (defensin 4) (Ace. No. AT5G44430).

Plants that can benefit from application of the composition of the subject invention include: Row Crops (e.g., Corn, Soy, Sorghum, Peanuts, Potatoes, etc.), Field Crops (e.g., Alfalfa, Wheat, Grains, etc.), Tree Crops (e.g., Walnuts, Almonds, Pecans, Hazelnuts, Pistachios, etc.), Citrus Crops (e.g., orange, lemon, grapefruit, etc.), Fruit Crops (e.g., apples, pears, etc.), Turf Crops, Ornamentals Crops (e.g., Flowers, vines, etc.), Vegetables (e.g., tomatoes, carrots, etc.), Vine Crops (e.g., Grapes, Strawberries, Blueberries, Blackberries, etc.).

The benefit can be in the form of, for example, increase yield, quality, disease and pest resistance, etc.

Plants that can benefit from the methods of the invention include all plants which belong to the superfamily Viridiplantae, in particular monocotyledonous and dicotyledonous plants including fodder or forage legumes, ornamental plants, food crops, trees or shrubs selected from the list comprising *Acer* spp., *Actinidia* spp., *Abelmoschus* spp., *Agave sisalana, Agropyron* spp., *Agrostis stolonifera, Allium* spp., *Amaranthus* spp., *Ammophila arenaria, Ananas comosus, Annona* spp., *Apium graveolens, Arachis* spp, *Artocarpus* spp., *Asparagus officinalis, Avena* spp. (e.g. *Avena sativa, Avena fatua, Avena byzantina, Avena fatua* var. *sativa, Avena hybrida*), *Averrhoa carambola, Bambusa* sp., *Benincasa hispida, Bertholletia excelsea, Beta vulgaris, Brassica* spp. (e.g. *Brassica napus, Brassica rapa* ssp. [canola, oilseed rape, turnip rape]), *Cadaba farinosa, Camellia sinensis, Canna indica, Cannabis sativa, Capsicum* spp., *Carex elata, Carica papaya, Carissa macrocarpa, Carya* spp., *Carthamus tinctorius, Castanea* spp., *Ceiba pentandra, Cichorium endivia, Cinnamomum* spp., *Citrullus lanatus, Citrus* spp., *Cocos* spp., *Coffea* spp., *Colocasia esculenta, Cola* spp., *Corchorus* sp., *Coriandrum sativum, Corylus* spp., *Crataegus* spp., *Crocus sativus, Cucurbita* spp., *Cucumis* spp., *Cynara* spp., *Daucus carota, Desmodium* spp., *Dimocarpus longan, Dioscorea* spp., *Diospyros* spp., *Echinochloa* spp., *Elaeis* (e.g. *Elaeis guineensis, Elaeis oleifera*), *Eleusine coracana, Eragrostis tef, Erianthus* sp., *Eriobotrya japonica, Eucalyptus* sp., *Eugenia uniflora, Fagopyrum* spp., *Fagus* spp., *Festuca arundinacea, Ficus carica, Fortunella* spp., *Fragaria* spp., *Ginkgo biloba, Glycine* spp. (e.g. *Glycine max, Soja hispida* or *Soja max*), *Gossypium hirsutum, Helianthus* spp. (e.g. *Helianthus annuus*), *Hemerocallis fulva, Hibiscus* spp., *Hordeum* spp. (e.g. *Hordeum vulgare*), *Ipomoea batatas, Juglans* spp., *Lactuca sativa, Lathyrus* spp., *Lens culinaris, Linum usitatissimum, Litchi chinensis*, Lotus spp., Luffa *acutangula, Lupinus* spp., *Luzula sylvatica, Lycopersicon* spp. (e.g. *Lycopersicon esculentum, Lycopersicon lycopersicum, Lycopersicon pyriforme*), *Macrotyloma* spp., *Malus* spp., *Malpighia emarginata, Mammea americana, Mangifera indica, Manihot* spp., *Manilkara zapota, Medicago sativa, Melilotus* spp., *Mentha* spp., *Miscanthus sinensis, Momordica* spp., *Morus nigra, Musa* spp., *Nicotiana* spp., *Olea* spp., *Opuntia* spp., *Ornithopus* spp., *Oryza* spp. (e.g. *Oryza sativa, Oryza latifolia*), *Panicum miliaceum, Panicum virgatum, Passiflora edulis, Pastinaca sativa, Pennisetum* sp., *Persea* spp., *Petroselinum crispum, Phalaris arundinacea, Phaseolus* spp., *Phleum pratense, Phoenix* spp., *Phragmites australis, Physalis* spp., *Pinus* spp., *Pistacia vera, Pisum* spp., *Poa* spp., *Populus* spp., *Prosopis* spp., *Prunus* spp., *Psidium* spp., *Punica granatum, Pyrus communis, Quercus* spp., *Raphanus sativus, Rheum rhabarbarum, Ribes* spp., *Ricinus communis, Rubus* spp., *Saccharum* spp., *Salix* sp., *Sambucus* spp., *Secale cereale, Sesamum* spp., *Sinapis* sp., *Solanum* spp. (e.g. *Solanum tuberosum, Solanum integrifolium* or *Solanum lycopersicum*), *Sorghum bicolor, Spinacia* spp., *Syzygium* spp., *Tagetes* spp., *Tamarindus indica, Theobroma cacao, Trifolium* spp., *Tripsacum dactyloides, Triticosecale rimpaui, Triticum* spp. (e.g. *Triticum aestivum, Triticum durum, Triticum turgidum, Triticum hybernum, Triticum macha, Triticum sativum, Triticum monococcum* or *Triticum vulgare*), *Tropaeolum minus, Tropaeolum majus, Vaccinium* spp., *Vicia* spp., *Vigna* spp., *Viola odorata, Vitis* spp., *Zea mays, Zizania palustris, Ziziphus* spp., amongst others.

The embodiments may be used for transformation of any plant species, including, but not limited to, monocots and dicots. Examples of plants of interest include, but are not limited to, corn (*Zea mays*), *Brassica* sp. (e.g., *B. napus, B. rapa, B. juncea*), particularly those *Brassica* species useful as sources of seed oil, alfalfa (*Medicago sativa*), rice (*Oryza sativa*), rye (*Secale cereale*), sorghum (*Sorghum bicolor, Sorghum vulgare*), millet (e.g., pearl millet (*Pennisetum glaucum*), proso millet (*Panicum miliaceum*), foxtail millet (*Setaria italica*), finger millet (*Eleusine coracana*)), sunflower (*Helianthus annuus*), safflower (*Carthamus tinctorius*), wheat (*Triticum aestivum*), soybean (*Glycine max*), tobacco (*Nicotiana tabacum*), potato (*Solanum tuberosum*), peanuts (*Arachis hypogaea*), cotton (*Gossypium barbadense, Gossypium hirsutum*), sweet potato (*Ipomoea batatus*), cassava (*Manihot esculenta*), coffee (*Coffea* spp.), coconut (*Cocos nucifera*), pineapple (*Ananas comosus*), citrus trees (*Citrus* spp.), cocoa (*Theobroma cacao*), tea (*Camellia sinensis*), banana (*Musa* spp.), avocado (*Persea americana*), fig (*Ficus casica*), guava (*Psidium guajava*), mango (*Mangifera indica*), olive (*Olea europaea*), papaya (*Carica papaya*), cashew (*Anacardium occidentale*), macadamia (*Macadamia integrifolia*), almond (*Prunus amygdalus*), sugar beets (*Beta vulgaris*), sugarcane (*Saccharum* spp.), oats, barley, vegetables, ornamentals, and conifers.

Vegetables include tomatoes (*Lycopersicon esculentum*), lettuce (e.g., *Lactuca sativa*), green beans (*Phaseolus vulgaris*), lima beans (*Phaseolus limensis*), peas (*Lathyrus* spp.), and members of the genus *Cucumis* such as cucumber (*C. sativus*), cantaloupe (*C. cantalupensis*), and musk melon (*C. melo*). Ornamentals include azalea (*Rhododendron* spp.), hydrangea (*Macrophylla hydrangea*), hibiscus (*Hibiscus rosasanensis*), roses (*Rosa* spp.), tulips (*Tulipa* spp.), daffodils (*Narcissus* spp.), petunias (*Petunia hybrida*), carnation (*Dianthus caryophyllus*), poinsettia (*Euphorbia pulcherrima*), and chrysanthemum. Conifers that may be employed in practicing the embodiments include, for example, pines such as loblolly pine (*Pinus taeda*), slash pine (*Pinus elliotii*), ponderosa pine (*Pinus ponderosa*), lodgepole pine (*Pinus contorta*), and Monterey pine (*Pinus radiata*); Douglas-fir (*Pseudotsuga menziesii*); Western hemlock (*Tsuga canadensis*); Sitka spruce (*Picea glauca*); redwood (*Sequoia sempervirens*); true firs such as silver fir (*Abies amabilis*) and balsam fir (*Abies balsamea*); and cedars such as Western red cedar (*Thuja plicata*) and Alaska yellow-cedar (*Chamaecyparis nootkatensis*). Plants of the embodiments include crop plants (for example, corn, alfalfa, sunflower, *Brassica*, soybean, cotton, safflower, peanut, sorghum, wheat, millet, tobacco, etc.), such as corn and soybean plants.

Turfgrasses include, but are not limited to: annual bluegrass (*Poa annua*); annual ryegrass (*Lolium multiflorum*); Canada bluegrass (*Poa compressa*); Chewings fescue (*Festuca rubra*); colonial bentgrass (*Agrostis tenuis*); creeping bentgrass (*Agrostis palustris*); crested wheatgrass (*Agropyron desertorum*); fairway wheatgrass (*Agropyron cristatum*); hard fescue (*Festuca longifolia*); Kentucky bluegrass (*Poa pratensis*); orchardgrass (*Dactylis glomerate*); perennial ryegrass (*Lolium perenne*); red fescue (*Festuca rubra*); redtop (*Agrostis alba*); rough bluegrass (*Poa trivialis*); sheep fescue (*Festuca ovine*); smooth bromegrass (*Bromus inermis*); tall fescue (*Festuca arundinacea*); timothy (*Phleum pretense*); velvet bentgrass (*Agrostis canine*); weeping alkaligrass (*Puccinellia distans*); western wheatgrass (*Agropyron smithii*); Bermuda grass (*Cynodon* spp.); St. Augustine grass (*Stenotaphrum secundatum*); zoysia grass (*Zoysia* spp.); Bahia grass (*Paspalum notatum*); carpet grass (*Axonopus affinis*); centipede grass (*Eremochloa ophiuroides*); kikuyu grass (*Pennisetum clandesinum*); seashore paspalum (*Paspalum vaginatum*); blue gramma (*Bouteloua gracilis*); buffalo grass (*Buchloe dactyloids*); sideoats gramma (*Bouteloua curtipendula*).

Plants of interest include grain plants that provide seeds of interest, oil-seed plants, and leguminous plants. Seeds of interest include grain seeds, such as corn, wheat, barley, rice, sorghum, rye, millet, etc. Oil-seed plants include cotton, soybean, safflower, sunflower, *Brassica*, maize, alfalfa, palm, coconut, flax, castor, olive etc. Leguminous plants include beans and peas.

Beans include guar, locust bean, fenugreek, soybean, garden beans, cowpea, mungbean, lima bean, fava bean, lentils, chickpea, etc.

The compositions and methods of the subject invention can be used to reduce damage caused by a wide range of pests.

Examples of the classification of pests include Lepidoptera (for example, Plutellidae, Noctuidae, Pyralidae, Tortricidae, Lyonetiidae, Carposinidae, Gelechiidae, Crambidae, Arctiidae, and Lymantriidae), Hemiptera (for example, Cicadellidae, Delphacidae, Psyllidae, Aphididae, Aleyrodidae, Orthezidae, Miridae, Tingidae, Pentatomidae, and Lygaiedae), Coleoptera (for example, Scarabaeidae, Elateridae, Coccinellidae, Cerambycidae, Chrysomelidae, and Curculionidae), Diptera (for example, Muscidae, Calliphoridae, Sarcophagidae, Anthomyiidae, Tephritidae, Opomyzoidea, and Carnoidea), Orthoptera (for example, Acrididae, Catantopidae, and Pyrgomorphidae), Thysanoptera (for example, Thripidae, Aeolothripidae, and Merothripidae), Tylenchida (for example, Aphelenchoididae and Neotylechidae), Collembola (for example, Onychiurus and Isotomidae), Acarina (for example, Tetranychidae, Dermanyssidae, Acaridae, and Sarcoptidae), Stylommatophora (for example, Philomycidae and Bradybaenidae), Ascaridida (for example, Ascaridida and Anisakidae), Opisthorchiida, Strigeidida, Blattodea (for example, Blaberidae, Cryptocercidae, and Panesthiidae) and Thysanura (for example, Lepismatidae, Lepidotrichidae, and Nicoletiidae).

Examples of the pests belonging to Lepidoptera include *Chilo suppressalis* Walker, *Cnaphalocrocis medinalis, Parnara guttata, Sesamia inferens, Mythimna separata, Naranga aenescens* Moore, *Spodoptera litura, Etiella zinckenella, Etiella behrii, Matsumuraeses falcana, Leguminivora glycinivorella, Pleuroptya naafis, Agrotis segetum, Agrotis ipsilon, Helcystogramma triannulellum, Xestia c-nigrum, Helicoverpa assulta, Helicoverpa armigera, Mamestra brassicae, Spodoptera exigua, Plutella xylostella, Pieris rapae, Pieris brassicae, Hellulla undalis*, and *Autographa nigrisigna*.

Examples of the pests belonging to Hemiptera include *Nilaparvata lugens, Sogatella furcifera, Laodelphax stratella, Nephotettix cincticeps, Recilia dorsalis, Stenotus rubrovittatus, Trigonotylus caelestialium, Leptocorisa chinensis, Nezara antennata, Nezara viridula, Lagynotomus elongatus, Scotinophara lurida, Eysarcoris annamita, Eysarcoris lewisi, Eysarcoris ventralis, Togo hemipterus* Scott, *Cletus punctiger, Piezodorus hybneri, Halyomorpha halys, Dolycoris baccarum, Neotoxoptera formosana, Rhopalosiphum padi, Rhopalosiphum maidis*, and *Aphis glycines*.

Examples of the pests belonging to Coleoptera include rice *Lissorhoptrus oryzophilus, Oulema oryzae, Echinocnemus squameus, Melanotus legatus, Melanotus fortnumi, Anomala cuprea, Popillia japonica, Maladera castanea, Epilachna varivestis, Paraluperodes nigrobilineatus, Epilachna vigintioctomaculata, Henosepilachna vigintioc-*

*topunctata, Harmonia axyridis, Anomala rufocuprea, Anomala testaceipes, Aulacophora indica*, and *Phyllotreta striolata*.

Examples of the pests belonging to Diptera include *Chlorops oryzae, Hydrellia griseola, Sitodiplosis mosellana, Delia platura, Asphondylia yushimai, Melanagromyza sojae, Liriomyza trifolii, Liriomyza sativae, Liriomyza huidobrensis*, and *Liriomyza bryoniae*.

Examples of the pests belonging to Orthoptera include *Oxya yezoensis* and *Oxya japonica*. Examples of the pests belonging to Thysanoptera include Stenchaetothrips *biformis* and *Thrips palmi*. Examples of the pests belonging to Tylenchida include *Meloidogyne, Nematoda*, and *Heterodera*. Examples of the pests belonging to Collembola include *Onchiurus psuedamatus yagii* and *Onychiurus matsumotoi*. Examples of the pests belonging to Acarina include *Penthaleus major, Tetranychus urticae, Tetranychus kanzawai, Tyrophagus putrescentiae*, and *Tarsonemus bilobatus*. Examples of the pests belonging to Stylommatophora include *Helix* and Philomycidae. Examples of the pests belonging to Ascaridida include *Ascaris lumbricoide*. Examples of the pests belonging to Opisthorchiida include *Metagonimus yokogawai*. Examples of the pests belonging to Strigeidida include *Schistosoma japonicum*. Examples of the pests belonging to Blattodea include *Blattella germanica, Periplaneta fuliginosa, Periplaneta americana*, and *Blatta lateralis*. Examples of the pests belonging to Thysanura include *Ctenolepisma* and *Lepisma*.

In view of the technical features of the present invention and the technical common knowledge in this field, the coverage of the present invention (more specifically the pests to which the pest control method of the present invention is applicable) is wide. On the other hand, as shown in the below-described examples, the efficacy or effectiveness of the present invention was confirmed by the experiments on *Henosepilachna vigintioctopunctata* and *Harmonia axyridis* belonging to Coleoptera: Coccinellidae, *Oxya yezoensis* belonging to Orthoptera: Catantopidae, *Helicoverpa armigera* belonging to Lepidoptera: Noctuidae, and *Blatta lateralis* belonging to Blattodea: Blattidae as test insects. In consideration of the fact, though there is no intention to limit the coverage of the present invention, the present invention is preferably applied to the insects belonging to Coleoptera, Orthoptera, Lepidoptera, or Blattodea, and more preferably to the insects belonging to Coleoptera: Coccinellidae, Orthoptera: Catantopidae, Lepidoptera: Noctuidae, or Blattodea: Blattidae. Specific examples of the insects belonging to Coleoptera: Coccinellidae include *Henosepilachna vigintioctopunctata* and *Harmonia axyridis*, and specific examples of the insects belonging to Orthoptera: Catantopidae include *Oxya yezoensis*. Specific examples of the insects belonging to Lepidoptera: Noctuidae include *Helicoverpa armigera*, and specific examples of the insects belonging to Blattodea: Blattidae include *Blatta lateralis*.

In an exemplary embodiment, guayule extract prevents formation of root galls caused by nematodes such as root knot and cyst nematodes.

Advantageously, unlike conventional pesticides that control pests by killing, the compositions provided herein can, in some embodiments, control pests by regulating a plants' own signaling pathways that are typically controlled by auxin and other hormones involved in plant tissues, production of saponins and other glycosides, as well as the increase in root hairs.

In certain embodiments, the subject invention protects attacks on plants that can be biotic or abiotic in nature.

Non-limiting examples of biotic attacks include plant parasites, arthropods, animals, fungi, bacteria, nematodes, reptiles, mollusks, scorpions, and viruses. Abiotic attacks are caused by, for example, changes in physical environments that include, but are not limited to, temperature, salinity, light exposure, water quality, soil quality, and oxidation.

Exemplary trials have demonstrated that the guayule extract of the subject invention provides a basis for improving the control of cyst, root knot, and lesion nematodes.

Compositions provided herein can also, when applied at, for example, high doses, enhance the protection of dried plants from pests such as, for example, termites, wood borers, fungi, bacteria, and certain animal pests common to lumber, dried wood, dried roots, and dried fruits.

In one embodiment, the subject composition improves the health and productivity of plants undergoing water stress.

The composition of the subject invention can also be used to induce budding and/or flowering, including in marijuana plants.

In some embodiments, chemical barriers resulting from the genetic regulation achieved using the compositions and methods of the subject invention include, but are not limited to, antagonistic compounds such as phytoalexins, fumigating compounds, and compounds that can alter the taste, smell, and/or pheromone characteristics of the plant.

In certain embodiments, the genetic and/or hormonal regulations are effective In inhibiting a pest's ability to find, penetrate, and/or consume the target plant. Further, the subject compositions, comprising the subject extracts and, optionally, other naturally derived additives, can interfere with a pest's ability to find a mate.

In some embodiments, the exogenous attacks are abiotic in nature, originating from extreme physical conditions that include, but are not limited to, changes in temperature, light exposure, water, soil, and other factors affecting the target plant's growth.

In some embodiments, the compositions provided herein, either in a dry or in liquid formulation, are applied as a seed treatment or to the soil surface.

Preferred methods include applying the compositions provided herein to the soil surface without mechanical incorporation. The pesticidal effect of the soil application can then be activated by rainfall, sprinkler, flood, or drip irrigation, and subsequently delivered to the targeted pests in order to drive their population levels down to acceptable thresholds. In an exemplary embodiment, the compositions provided herein can be efficiently applied via a center pivot irrigation system or with a spray over the seed furrow.

Reference herein to administration of the composition "on or near" a pest or a plant or to the "environment" of a pest or plant means that the administration is such that the composition is sufficiently in contact with the pest or plant such that the desired result (e.g., killing the pest, increasing yield, preventing damage to the plant, regulating genes and/or hormones, etc.) is achieved.

Use of the term "comprising," herein includes consisting essentially of" and "consisting of." The term "consisting essentially of," as used herein, limits the scope of the ingredients and steps to the specified materials or steps and those that do not materially affect the basic and novel characteristic(s) of the present invention, e.g., compositions and methods for promoting plant health via hormones and/or gene regulation and/or pest control.

Advantageously, the compositions provided herein using, for example, compositions extracted from desert shrubs of guayule plants, are cost-effective, especially when compared with synthetic counterparts. For example, based on current evidence and knowledge of efficacy and application rates, for a low concentration extract from guayule plants, worldwide control of cyst nematodes could be accomplished with several thousand acres of guayule production.

EXAMPLES

It should be understood that the examples and embodiments described herein are for illustrative purposes only and that various modifications or changes in light thereof will be suggested to persons skilled in the art and are to be included within the spirit and purview of this application.

Example 1

In an exemplary embodiment, a method of extracting and packaging a composition for plant growth and defense treatment, as described herein, includes the following steps.

First, parts of the source plant such as roots or shoots are cleaned of excessive dirt by rinsing or by physical brushing, followed by a treatment with $H_2O_2$ to remove mold, if appropriate. The source plant's roots or shoots then are sized with shears to fit into a grinder, which grinds the plant parts into a powder. Alternatively, the plant parts are wet ground in one or more solvents such as water, ethanol, propanol, isopropanol, *Quillaja saponaria* extracts, or *Yucca schidigera* extracts. Then the powder can be stored in a sealed container and refrigerated.

To make a 10% plant extract solution, 10 g of dry root powder is added to 90 g of distilled water or other solvent as provided earlier in this Example. In certain embodiments, 50%, 40%, 25%, or 10% or less of the total solvent is non-water. Other concentrations can be made by adjusting the mass of the plant extracts to the total solvent volume. The plant extracts and the solvent mixture can be stored covered and refrigerated for 48 hours while being stirred every 4 to 6 hours. The mixture is then decanted and filtered through stacked paper filters (4 filters/stack).

In one embodiment, the extract is tested for one or more of the activities described herein. The web plant bagasse can be pressed to obtain additional plant extracts and filtered through stacked paper filters (4 filters/stack). The filtered solution, with, optionally, added antioxidant, is then placed in UV-protected bottles. It is preferable that the bottles are filled to the rim in order to exclude air in the packaging.

For commercial production methods of extract and processing have been developed for larger volumes of Guayule and other plant extracts without the use of hexanes or alcohols but rather through water processing.

One specific example of a production method is as follows:

Iso-Extract Production-Line Steps:
1. Root Harvest Timing: Root quality is sampled in the field, utilizing a horizontal sampling technique (e.g., every $5^{th}$ row across and 20 feet vertically), providing 24 root samples over a 400 Ft×480 Ft field. Samples can be collected, for example, in the months of February, May, August, and November, cleaned, ground, and sample extractions produced and tested for the presence and quantity of specified chemical markers. Root is harvested when chemical markers are present in the amounts specified for formulations. Medium size roots are cut and removed.
2. Root Harvest: The weight of dry root needed for a production run is calculated and the acreage for harvest is determined. The root is harvested with the tops of the plants first removed, and then the dry root is extracted and bundled. The total sampled root amount would be near 100 roots. (96) roots. Preferably plants are not destroyed for a sample. Harvested root is preferably stored in a shaded commodity barn until processed.
3. Preliminary Root Processing: Dry root from the field is first cleaned in a tumbler with a well water rinse. Well water is used for the rinse, filtered, and re-circulated, with the sediment material periodically removed and deposited in the surrounding fields.
4. Preliminary Sizing: The cleaned dry root is conveyored into a preliminary sizer-chipper, and sized to <1 inch lengths.
5. Wet Grind: The chipped-sized root is weighed and then fed into a wet mill via an auger. Microbial-free water is added to the auger and chipped root and ground to an average particle size of less than $\frac{1}{16}$ inch to produce a pumpable slurry. Preferably, the particles pass through a ¼ inch, ⅛ inch or smaller screen size. The amount of water added can be, for example, from about 0.75 to 1.5 lbs of root per gallon of water. More preferably there is about 0.9 to about 1.25 lbs of root per gallon of water. Microbial-free RO water can be produced and stored on site.

The percentage of the extract as that term is used herein (e.g., 10% or 30%) refers to the weight of the plant part (e.g., root) as a percentage of the weight of the mixture of the plant part and the solvent (e.g., water) that is contacted with the plant part. The concentration may be, for example, 50%, 40%, 30%, 20%, 10% or less, and any percentage in between. Preferably, the concentration is about 30%. The volume of water metered into the grinder tank is slightly higher than the finished concentration sought. The volume of root chips is varied according to the crop age, date of harvest, moisture content, storage term, colorimeter test on extract, and other concentration measurement tools.

6. Transfer from Grinder to Press: The root-water slurry is pumped to a series of dwell tanks, and allowed to "sit" until a desired concentration of active components is achieved. The content of the composition can be evaluated using, for example, a GLC and mass-spectrometer. The concentration of the composition can also be determined based on colorimetry and/or specific gravity. When the proper composition of the Iso-Extract is achieved, the dwell tank(s) contents are pumped to a rotary press. The rotary press separates the Iso-Extracts solution from the bagasse, with the solution then pumped, filtered, and stored in a batch tank. The percentage of solids is preferably less than 5%, 4%, 3%, 2%, or 1%. The bagasse solids can be transferred out of the building and used in compost production. In preferred embodiments, solids larger than 16, 24, 32, 40, or 48 microns are removed. In further preferred embodiments, particles that do not fit through an ½ inch, ¼, inch or ⅛ inch screen are removed.
7. Batch Tank: The Iso-Extract solution can be again checked for concentration and composition using the GLC and mass-spectrometer. Should the solution concentration be too high, microbial-free RO water is added to the Iso-Extract solution to achieve the desired concentration. When the desired concentration is reached, 0.1% Sodium Benzoate by weight is added to the solution and the solution is then filtered and pumped through filtration into a series of storage tanks for use in the eventual production of formulations. The stored Iso-Extract composition and concentration can be periodically monitored to assure consistent maintenance of quality.

8. Production of Formulations and Bottling: Iso-Extract is pumped from the storage tanks, to a 2,500 gallon blending tank, where various additives are blended with the Iso-Extract, to produce specified formulations. Such additives, are weighed and manually added, the solution continually stirred, and then allowed to dwell as needed. The formulation's concentration and composition can be checked with a GLC and mass-spectrometer, and when correct, filtered and pumped to a filling station and placed in containers. Formulations can be shipped in tote-sized containers, or bottled (1 gallon and 2.5 gallon F-Style Jugs) with a rotary type, 16 head filler, capped, labeled, and cased. Cases are placed on a pallet, shrink wrapped, and either stored, or immediately shipped. The additives can be, for example, plant nutrients, organic and conventionally derived plant fertility products and saponins (wetting agents).

9. Product Storage and Distribution: Package product is palleted and placed in inventory for sale. Bulk product is placed in 270 gallon totes. Depending on volume produced, the pallets/totes can be stored onsite, or transported to a separate warehouse for storage and shipping.

Example 2

Trials were conducted using the compositions and methods provided herein. Advantageously, the results were better than fumigation with Telone II or Vapam.

The efficacy of the guayule extract on sugar beet cyst nematodes was demonstrated. Additionally, the same aqueous extract of the guayule roots was used to treat broccoli cyst nematodes. It, too, was successful in increasing the crop yield and suppressing the growth of cyst nematode. The guayule extract was also tested on root knot nematodes grown on tomatoes, carrots, and melons. Significant yields and reduction of the nematode population were observed.

Furthermore, guayule plants were direct-seeded on rows next to a test site. These rows were next to heavily infested tomato plants of that growing season. The root knot nematodes in this section were completely controlled.

Because of the Bt resistance buildup by corn root worms in the Midwest, this extract can be potentially useful for treating the 100 million acres of corn grown in the United States and beyond.

Additional experimental results have demonstrated effective control or parasitic nematodes such as cyst nematodes, *Heterodear schactii*, and *Heterodera cruciferi* in sugar beets and broccoli plants with positive benefits to crop yield, soil health, and recovery of beneficial nematodes. Advantageously, the beneficial nematode population was found to increase shortly after the application of the compositions of the subject invention.

Example 3

In an exemplary embodiment, a composition for regulating a target plant's genes and/or hormones comprises one or more of the following: acetic acid, abscisic acid, acc-synthases, acetovallinones, argentatins, brassinoles, caffeic acid, campesterol, camphene, carvacrol, cis-cinnamic acid, trans-cinnamic acid, cholorgenic acid, d-limonene, eugenol, galactooligosaccharide, gemional, guaiacol, guayulins, gibberellic acids, indole, inulins, lignins, iodine, jasmonic acid, jasmonates, kaempferol, kaempferol 3 methyl ether, kaempferol 2-glycoside, kinetin, limonene, linoleic acid, linolenic acid, lupenes, melavonic acid, myrcene, naringenin, oleic acid, palmitic acid, p-anlSIC acid, pinenes, pulegones, qualyins, quercetagetin, quercetins, quinic acid, saponins, salicylic acid, sanquarinine, stearic acid, thymol, trehalose 6-phosphate (Tre6P), terpenes, tri-terpenois, turpines, vanillins, and zeatin. 3,4-dihydroxyhydrocinnamic acid, 3-hydropropionic acid along with latex/rubber transferase enzymes such as cysteine protease, aspartate protease, histidine protease and one or more other proteases derived from Guayule parenchyma cell latex and rubber. Reference here to these enzymes includes the induction of these enzymes (or other enzymes) in the plant as consequence of applying the subject composition).

Example 4—Analysis of Guayule Iso Root Extract 30% Top 30 Compounds Detected in Mass Spectrometer Readings

TABLE 1

| Number | Bin | Chemical Compound Base | Name | C Iso-Extract 30% Root Extract 3% (Dilute) | B Iso-Extract 10% Root Extract 1.0% (Dilute) | A Iso-Extract 5% Root Extract 0.5% (Dilute) |
|---|---|---|---|---|---|---|
| 1 | | | ornithine | 834607 | 550417 | 920681 |
| 2 | | | butane-2,3-diol NIST | 655045 | 1123855 | 488756 |
| 3 | | | alanine | 339330 | 296759 | 226593 |
| 4 | | | erythritol | 295742 | 356978 | 255760 |
| 5 | | | mannitol | 221692 | 10718 | 6280 |
| 6 | | | lyxitol | 215468 | 7658 | 431018 |
| 7 | | | valine | 211756 | 118514 | 101846 |
| 8 | | | quinic acid | 204775 | 18488 | 328697 |
| 9 | | | 3-hydroxypropionic acid | 195680 | 335152 | 4360 |
| 10 | | | phenylethylamine | 183461 | 159590 | 100394 |
| 11 | | | succinic acid | 177648 | 275226 | 168678 |
| 12 | | | 6-deoxyglucose | 168205 | 1885 | 195877 |
| 13 | | | glycine | 164987 | 118641 | 59105 |
| 14 | | | myo-inositol | 139850 | 211557 | 200211 |
| 15 | | | lactic acid | 136912 | 394295 | 302238 |
| 16 | | | glutamic acid | 123068 | 56176 | 48647 |
| 17 | | | aspartic acid | 116113 | 33766 | 25798 |
| 18 | | | putrescine | 112926 | 398439 | 399490 |

TABLE 1-continued

| | | | C<br>Iso-Extract<br>30%<br>Root Extract | B<br>Iso-Extract<br>10%<br>Root Extract | A<br>Iso-Extract<br>5%<br>Root Extract |
|---|---|---|---|---|---|
| | Chemical Compound | | | | |
| Number | Bin | Base Name | 3% (Dilute) | 1.0% (Dilute) | 0.5% (Dilute) |
| 19 | | isoleucine | 108844 | 38670 | 33831 |
| 20 | | propane-1,3-diol NIST | 108234 | 137437 | 2950 |
| 21 | | tyrosine | 107965 | 36997 | 44736 |
| 22 | | oxoproline | 99114 | 80004 | 61687 |
| 23 | | histidine | 64564 | 50767 | 42943 |
| 24 | | phosphate | 52985 | 131940 | 169923 |
| 25 | | 3,4-dihydroxycinnamic acid | 52338 | 12193 | 52457 |
| 26 | | N-methylalanine | 50107 | 81638 | 65694 |
| 27 | | uridine | 48451 | 35345 | 46423 |
| 28 | | ribonic acid | 31228 | 10825 | 15024 |
| 29 | | glycerol | 19271 | 32607 | 669969 |
| 30 | | urea | 16694 | 24503 | 30177 |

The composition preferably contains at least 5, 10, 15, 20, 25 or all 30 of these compounds.

Example 5—Control of Cyst Nematode

Control of cyst nematode was comparable to standard fumigation and other contact nematicides.
  Objective: Evaluate nematicides for sugarbeet cyst nematode control and subsequent growth of sugarbeets
  Type: Cyst Nematode Control
  Crop: Sugar Beets
  Variety: *Phoenix*, Coronado, Baja, Cortez, SV2013, SV2015, Beta 4521R, Beta 4430R, Beta 8520, and Beta 8617.
  Plot Design: Randomized Block
  Plot Size: 25' Long×3.3' Wide
  Replicates: 6
  Soil Type: Sandy Loam
  Soil Notes: Desert Sand
  Irrigation Method: Drip Irrigation
Major Event Dates:

| Pre Application | Sep 25$^{th}$ | (Telone Injection Preplant) |
|---|---|---|
| Planting | Oct 16$^{th}$ | (Planting) |
| First Application | Oct 16$^{th}$ | (All Treatments Applied at Transplanting) |
| Second Application | Oct 30$^{th}$ | (Treatments 5-7, 15-18, & 20 Re-Applied) |
| Harvest | Apr 22$^{nd}$ | (All plots harvested & Nematode samples collected) |

Application Information:

| 1) | Untreated Check UTC |
|---|---|
| 2) | Telone II (1,3-Dichloropropene) |
| 3) | Nimitz liquid |
| 4) | Nimitz granules |
| 5) | Stimulate (IBA, GA3 and cytokinin, Stoller Enterprises, Houston, TX) |
| 6) | More Power (Calcium Chloride and amino acids, Stoller Enterprises, Houston, TX) |
| 7) | Root Power (micronutrients and amino acids, Stoller Enterprises, Houston, TX) |
| 8) | Cortez Resistant Seed |
| 9) | SV2013 Resistant Seed |
| 10) | Baja Resistant Seed |
| 11) | Beta 4430R Resistant Seed |
| 12) | Beta 4521R Resistant Seed |
| 13) | Beta 8617 Resistant Seed |
| 14) | Beta 8520 Resistant Seed |
| 15) | LM0624 (wetting agent plus amino acids, Beem Consulting, Sacramento, CA) |
| 16) | GWN 10221 (mixture of biologicals, Gowan, Yuma, AZ) |
| 17) | GWN 1535 (Neem, Gowan, Yuma, AZ) |
| 18) | GU7812 (GU 30% extract, Beem Biologics, Sacramento, CA) |
| 19) | SV2015 Resistant Seed |
| 20) | Transformer (citrus wetting agent and boric acid, ORO AGRI, Fresno, CA) |
| 21) | Coronado Resistant Seed |

Application Method: Telone II was injected as a Fumigant in the soil 3 weeks before planting. The remainder of the treatments were applied over the top of the soil in a 1 foot band on a 3.33 ft wide bed, at planting and two weeks after.

Notes Rate of App: The rates are based on broadcast acre but were banded at 40% of the bed over the center 1 foot area over the seed line and thereafter over the top of the emerged seedling two weeks later. Therefore although the rates Indicate 1 pt or 2 pt/acre. The total amount of material per acre was reduced 60%. Thus actual amounts of product used was less than 1 pt per acre. It was 5.0 oz used per acre. 2 applications would be 10 oz./A Maintenance App: Standard herbicide, hand hoeing, and fertilizers were used during the course of this trial.

Evaluation Methods: Beets were hand dug from each replicate and analyzed. For analysis, the pounds per sugarbeet was converted to tons/acre based on a 40 inch row spacing and a 5 inch spacing in the row between sugarbeets. Nematode samples were taken from each replicate, and analyzed for juveniles of sugarbeet cyst nematode.

Statistical Analysis: Analysis of Variance (ANOVA) followed by Fisher's Least Significant Difference Test.

Objectives and Progress: A trial consisted of 21 treatments in a randomized complete block design with 6 replicates per treatment. A standard treatment of Telone II at 9 gpa was applied on September 25. The trial was planted and remaining treatments were applied October 16, followed by irrigation on the same day. The Telone II treatment, untreated control, and ten new product treatments were planted. The new product treatments were: LM0624 (wetting agent plus amino acids, Beem Consulting, Sacramento, CA), GWN 10221 (mixture of biologicals, Gowan, Yuma, AZ), GWN 1535 (Neem, Gowan, Yuma, AZ), GU7812 (GU 30% Beem Biologics, Sacramento, CA), Transformer (citrus wetting agent and boric acid, ORO AGRI, Fresno, CA), Stimulate (IBA, GA3 and cytokinin, Stoller Enterprises, Houston, TX), More Power (Calcium Chloride and amino acids, Stoller Enterprises, Houston, TX), Root Power (micronutrients and amino acids, Stoller Enterprises, Houston, TX), Nimitz (MCW-2, fluensulfone, ADAMA, Raleigh, NC), and Nimitz (MCW-2, fluensulfone) granules.

The varieties tested were: *Phoenix*, Coronado, Baja, Cortez, SV2013, SV2015, Beta 4521R, Beta 4430R, Beta 8520, and Beta 8617.

The trial was harvested on April 22.

Beets were hand dug from each replicate and analyzed. For analysis, the pounds per sugarbeet determined from the Spreckels laboratory data for Clean Beets was converted to tons/acre based on a 40 inch row spacing and a 5 inch spacing in the row between sugarbeets. Nematode samples were taken from each replicate, and analyzed for juveniles of sugarbeet cyst nematode.

Figure 2:
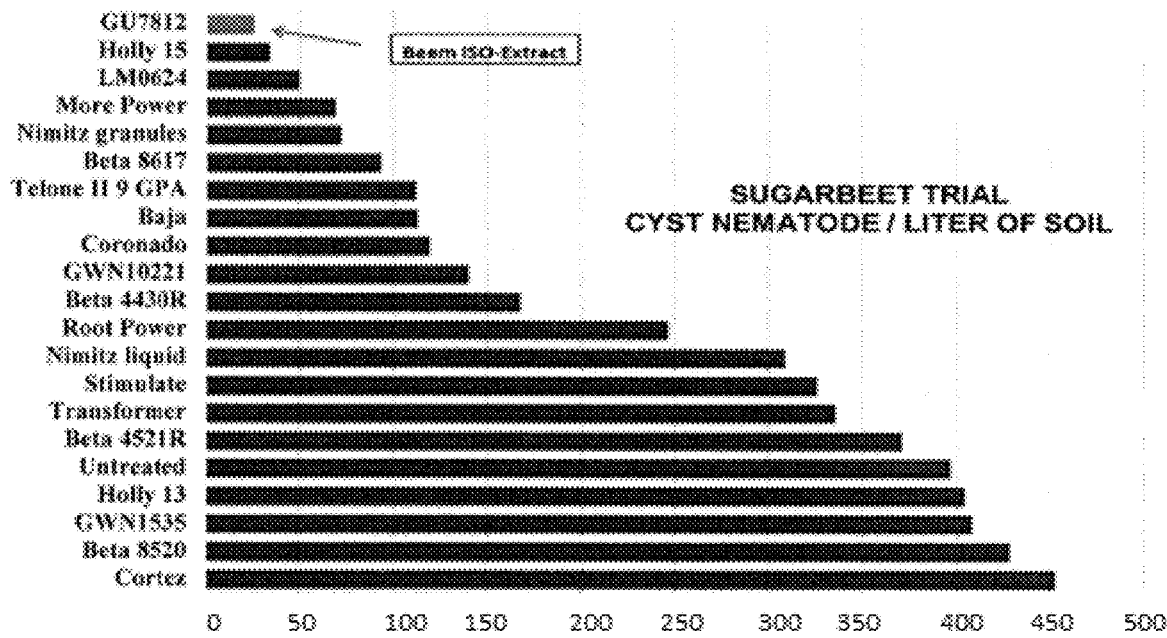
FIG. 2 shows a decrease in cyst nematodes.

ISO-EXTRACT GU 30% (GU7812) gave the greatest reduction in Cyst Nematode and nearly the highest increase in Sugar Beet yield. The yield was higher than the Telone II fumigation standard. (See FIGS. 1 and 2)

TABLE 3

Cyst nematode data for the sugarbeet trial

| | Cyst Nematode Juveniles/Liters of Soil | | | |
|---|---|---|---|---|
| | | | Log | |
| Treatment | 0.05 | 0.1 | 0.05 | 0.1 |
| 1 Untreated | 396.67 AB | ABCD | AB | AB |
| 2 Telone II 9 GPA | 112.00 AB | BCDEF | ABC | ABCD |
| 3 Nimitz liquid | 309.00 AB | ABCDEF | ABC | ABCD |
| 4 Nimitz granules | 72.67 AB | BCDEF | ABC | ABCD |
| 5 Stimulate | 326.00 AB | ABCDEF | ABC | ABCD |
| 6 More Power | 70.00 AB | CDEF | ABC | ABCD |
| 7 Root Power | 246.6 AB | ABCDEF | ABC | AB |
| 8 Cortez | 453.00 A | A | AB | AB |
| 9 SV2013 | 404.00 AB | ABCD | ABC | ABCD |
| 10 Baja | 112.80 AB | ABCDEF | ABC | ABCD |
| 11 Beta 4430R | 168.00 AB | ABCDEF | ABC | ABCD |
| 12 Beta 4521R | 370.67 AB | ABCDE | ABC | ABCD |
| 13 Beta 8617 | 93.33 AB | BCDEF | ABC | ABCD |
| 14 Beta 8520 | 428.00 AB | AB | ABC | ABC |
| 15 LM0624 | 50.40 AB | DEF | ABC | ABCD |
| 16 GWN10221 | 140.67 AB | ABCDEF | BC | CD |
| 17 GWN1535 | 408.00 AB | ABC | ABC | AB |
| 18 GU7812 | 26.00 B | F | C | D |
| 19 SV2015 | 34.67 B | EF | ABC | BCD |
| 20 Transformer | 336.00 AB | ABCDEF | A | A |
| 21 Coronado | 119.33 AB | ABCDEF | ABC | ABCD |

TABLE 2

Harvest data for sugarbeet trial

| | Weight/Beet (lb) | | Tons/Acre | | Percent Sugar | |
|---|---|---|---|---|---|---|
| Treatment | 0.05 | 0.1 | 0.05 | 0.1 | 0.05 | 0.1 |
| 1 Untreated | 1.93 AB | ABCDE | 30.24 AB | ABCDE | 13.32 BCDE | CDEFG |
| 2 Telone II 9 GPA | 2.41 AB | ABCD | 37.73 AB | ABCD | 12.97 CDE | FG |
| 3 Nimitz liquid | 2.05 AB | ABCDE | 32.17 AB | ABCDE | 13.56 BCDE | BCDEFG |
| 4 Nimitz granules | 1.96 AB | ABCDE | 30.75 AB | ABCDE | 13.16 BCDE | EFG |
| 5 Stimulate | 1.87 AB | BCDE | 29.30 AB | BCDE | 14.51 ABCDE | BCDE |
| 6 More Power | 2.24 AB | ABCDE | 35.13 AB | ABCDE | 13.63 BCDE | BCDEFG |
| 7 Root Power | 1.64 BC | EF | 25.73 BC | EF | 14.01 BCDE | BCDEFG |
| 8 Cortez | 1.93 AB | ABCDE | 30.30 AB | ABCDE | 13.46 BCDE | BCDEFG |
| 9 SV2013 | 1.55 BC | EF | 24.29 BC | EF | 14.57 ABCDE | BCDE |
| 10 Baja | 2.12 AB | ABCDE | 33.22 AB | ABCDE | 12.83 E | G |
| 11 Beta 4430R | 1.81 ABC | CDE | 28.42 ABC | CDE | 13.29 BCDE | DEFG |
| 12 Beta 4521R | 1.79 ABC | DE | 28.00 ABC | DE | 14.40 ABCDE | BCDEF |
| 13 Beta 8617 | 2.61 A | A | 40.85 A | A | 14.52 ABCDE | BCDE |
| 14 Beta 8520 | 1.98 AB | ABCDE | 31.00 AB | ABCDE | 12.94 DE | FG |
| 15 LM0624 | 2.58 A | AB | 40.43 A | AB | 14.77 ABC | ABCD |
| 16 GWN10221 | 2.05 AB | ABCDE | 32.20 AB | ABCDE | 14.10 BCDE | BCDEFG |
| 17 GWN1535 | 1.84 AB | CDE | 28.80 AB | CDE | 13.66 BCDE | BCDEFG |
| 18 GU7812 | 2.52 A | ABC | 39.49 A | ABC | 14.73 ABCD | ABCD |
| 19 SV2015 | 1.76 ABC | DE | 27.52 ABC | DE | 14.87 AB | AB |
| 20 Transformer | 0.97 C | F | 15.26 C | F | 16.10 A | A |
| 21 Coronado | 2.15 AB | ABCDE | 33.68 AB | ABCDE | 14.89 AB | ABC |

Each figure is the mean of 6 replicates.
Means not followed by the same letter are significantly different from each other according to Fisher's Protected Least Significant Difference Test at P=0.05 or 0.10

Each figure is the mean of 6 replicates.
Means not followed by the same letter are significantly different from each other according to Fisher's Protected Least Significant Difference Test at P=0.05 or 0.10.

Example 6—Trial where Guayule Extract was Effective on Cyst Nematode in Sugar Beets In this trial the pressure of Cyst Nematode was made extremely high by growing susceptible crops as hosts in rotation during winter month for over 30 years.

Objective: Evaluate nematicides for sugarbeet cyst nematode control and subsequent growth of sugarbeets
Type: Nematode Control
Location: Irvine, California
Crop: Sugar Beets
Variety: *Phoenix* (Susceptible)
Plot Design: Randomized Block
Plot Size: 10'×2.5'
Replicates: 5
Soil Type: Sandy Loam

| Soil Notes: | Sand: | 66% |
| --- | --- | --- |
| | Silt: | 21% |
| | Clay: | 13% |
| | Organic Matter: | 0.60% |
| | pH: | 7.6 |
| | CEC: | 0.68 milimhos/cm |

Irrigation Method: Overhead Sprinklers followed by Drip Irrigation one month after established crop.
Major Event Dates:

| Fumigation Application | Jun 4$^{th}$ | (Telone Injection Preplant) |
| --- | --- | --- |
| Pre-plant Application | Jun 8$^{th}$ | (Nimitz Treatments Applied Preplant) |
| Planting | Jun 18$^{th}$ | (Seed Planting) |
| 1$^{st}$ Application | Jun 18$^{th}$ | (All Treatments Applied at time of Planting) |
| 2$^{nd}$ Application | Jul 2$^{nd}$ | (Repeat Applications for Treatments 2-9 & 11) |
| 3$^{rd}$ Application | July 16$^{th}$ | (Repeat Applications for Treatments 2-9 & 11) |
| Harvest | Oct 29$^{th}$ | (Harvest Date) |

Treatments: 1 Untreated
2 BG-T 1 pt/a
3 RP-T 1 pt/a
4 RaizeMore-T 2 pt/a
5 BBI GU 10% 1 pt/a
6 BBI GU 10% 3 pt/a
7 LM-2015 1 pt/a
8 Nema-Q 3 pt/a
9 BBI GU 10% &LM 1+1 pt/a
10 Diatomaceous Earth 30 lb/a
11 Nimitz+BG-T 3.5+1 pt/a
12 Nimitz 5 pt/a at plant
13 Nimitz 5 pt/a pre-plant
14 Nimitz 3.5 pt/a at plant
15 Nimitz 3.5 pt/a pre-plant
16 Telone 9 gpa
Harvest Date: October 29
Evaluation Methods: At harvest, 5 plants from each replicate were harvested and weighed. First sample taken at untreated preplant to establish presence of population. All replicates sampled at harvest, 12, 1 inch (2.5 cm) diameter cores per replicate to a 12 inch (30 cm) depth.
Application Notes: Applications were made as band applications over the top of the seed line in a 1 ft. band over center 2.5 ft. bed.
Statistical Analysis: Analysis of Variance (ANOVA) followed by Fisher's Least Significant Difference Test.

TABLE 4

Harvest Data for the Sugar Beet Trial

| | | | | Cyst nematode juveniles/liter of soil | | | | |
| --- | --- | --- | --- | --- | --- | --- | --- | --- |
| | Yield (Kg/5 Beets) | | | | | | log (X + 1) | |
| Treatment | | 0.05 | 0.1 | | 0.05 | 0.1 | 0.05 | 0.1 |
| 1 Untreated | 4.83 | B | B | 39.2 | AB | AB | A | A |
| 2 BG-T 1 pt/a | 5.10 | AB | B | 21.6 | AB | B | AB | ABC |
| 3 RP-T 1 pt/a | 6.48 | A | A | 49.6 | AB | AB | A | AB |
| 4 RaizeMore-T 2 pt/a | 5.40 | AB | AB | 8.0 | B | B | AB | BC |
| 5 BBI GU 10% 1 pt/a | 4.73 | B | B | 37.2 | AB | AB | AB | ABC |
| 6 BBI GU 10% 3 pt/a | 5.75 | AB | AB | 26.8 | AB | B | A | AB |
| 7 LM-2015 1 pt/a | 5.57 | AB | AB | 48.0 | AB | AB | AB | AB |
| 8 Nema-Q 3 pt/a | 5.79 | AB | AB | 50.8 | AB | AB | A | AB |
| 9 BBI GU 10% &LM 1 + 1 pt/a | 5.89 | AB | AB | 21.2 | AB | B | AB | AB |
| 10 Diatomaceous Earth 30 lb/a | 5.48 | AB | AB | 8.4 | B | B | B | C |
| 11 Nimitz + BG-T 3.5 + 1 pt/a | 4.74 | B | B | 25.2 | AB | B | AB | AB |
| 12 Nimitz 5 pt/a at plant | 4.90 | B | B | 57.6 | AB | AB | AB | AB |
| 13 Nimitz 5 pt/a pre-plant | 5.77 | AB | AB | 34.8 | AB | AB | AB | AB |
| 14 Nimitz 3.5 pt/a at plant | 5.65 | AB | AB | 17.2 | B | B | AB | ABC |
| 15 Nimitz 3.5 pt/a pre-plant | 5.82 | AB | AB | 86.0 | A | A | A | A |
| 16 Telone 9 GPA | 5.89 | AB | AB | 17.2 | B | B | AB | ABC |

Each figure is a mean of 5 replicates

Means not followed by the same letter are significantly different from each other according to Fisher's Protected Least Significant Difference Test at P = 0.05 or 0.10

Summary and Discussion:

The soil had been maintained to be highly infested with Cyst Nematode adults, larvae and eggs. The ISO EXTRACT GU 10% was applied at 1 pt/Acre and 3 pts/Acre to determine a dose response difference compared to the standard Telone II fumigation, other chemical nematicides and the untreated check.

Additionally, a combination of ISO EXTRACT GU 10% with a new wetting agent (LM 2015) was introduced. ISO EXTRACT GU 10% @ 3 pts/Acre, alone, performed very well and was comparable to the GU 30% formulation @ 1 pint/Acre in earlier trials. The GU 10% @ 1 pt/Acre was ⅓ less the amount of active molecules and was not sufficient for yield or nematode control.

Figure 3:
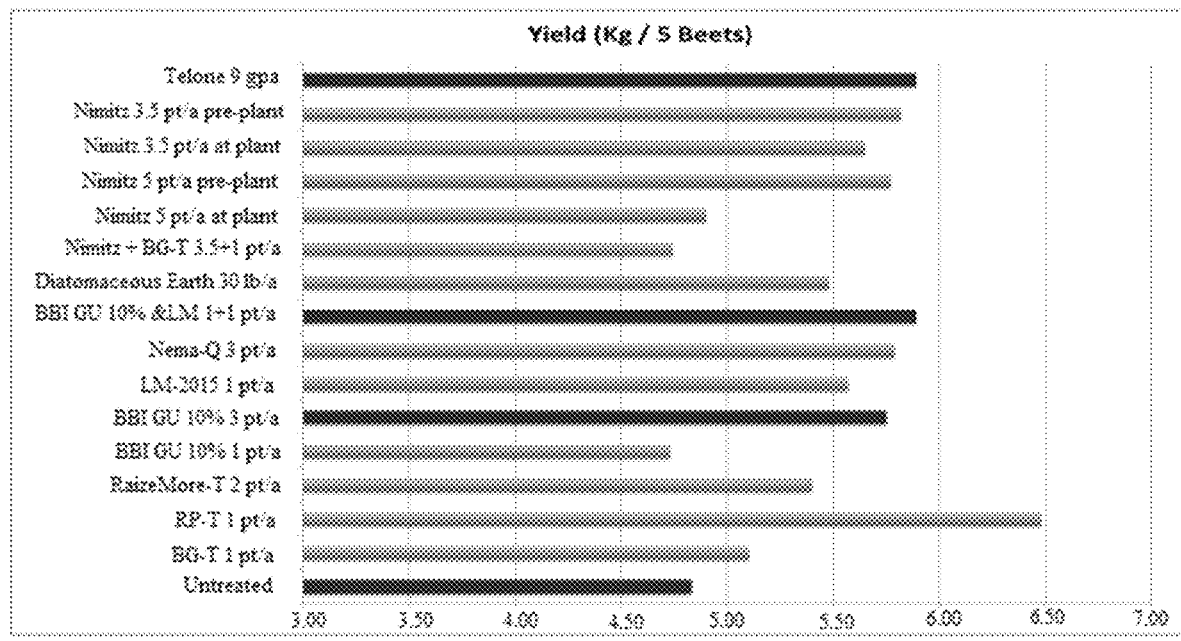
FIG. 3 shows increased sugarbeet yield.
Figure 4:
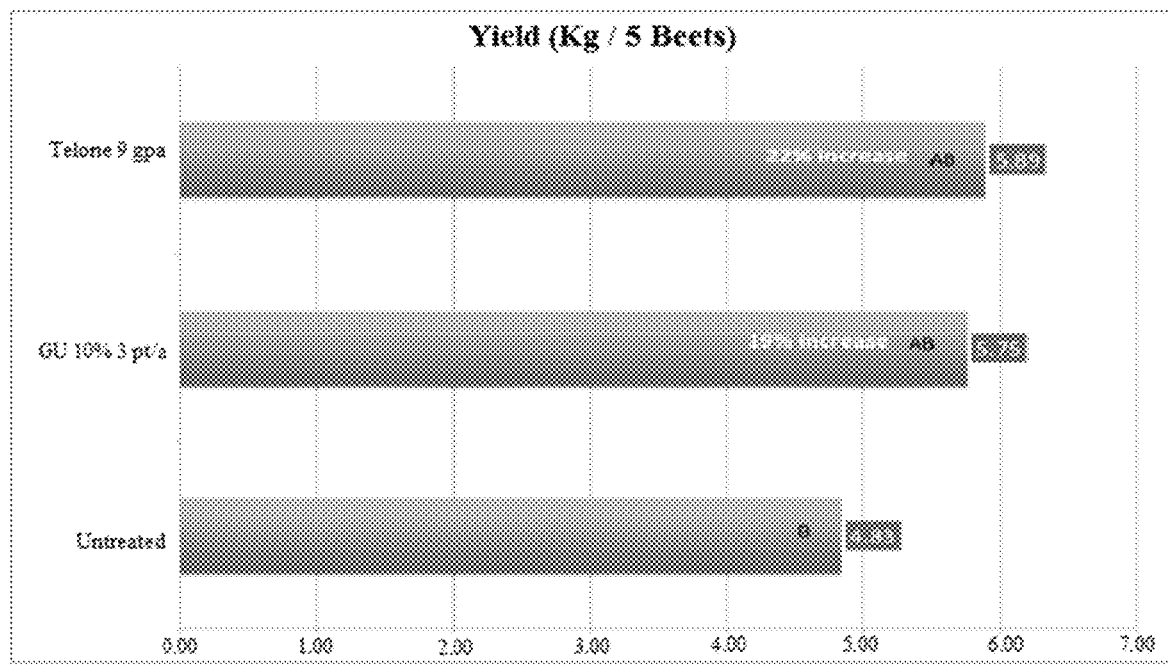
FIG. 4 shows increased sugarbeet yield.
Figure 5:
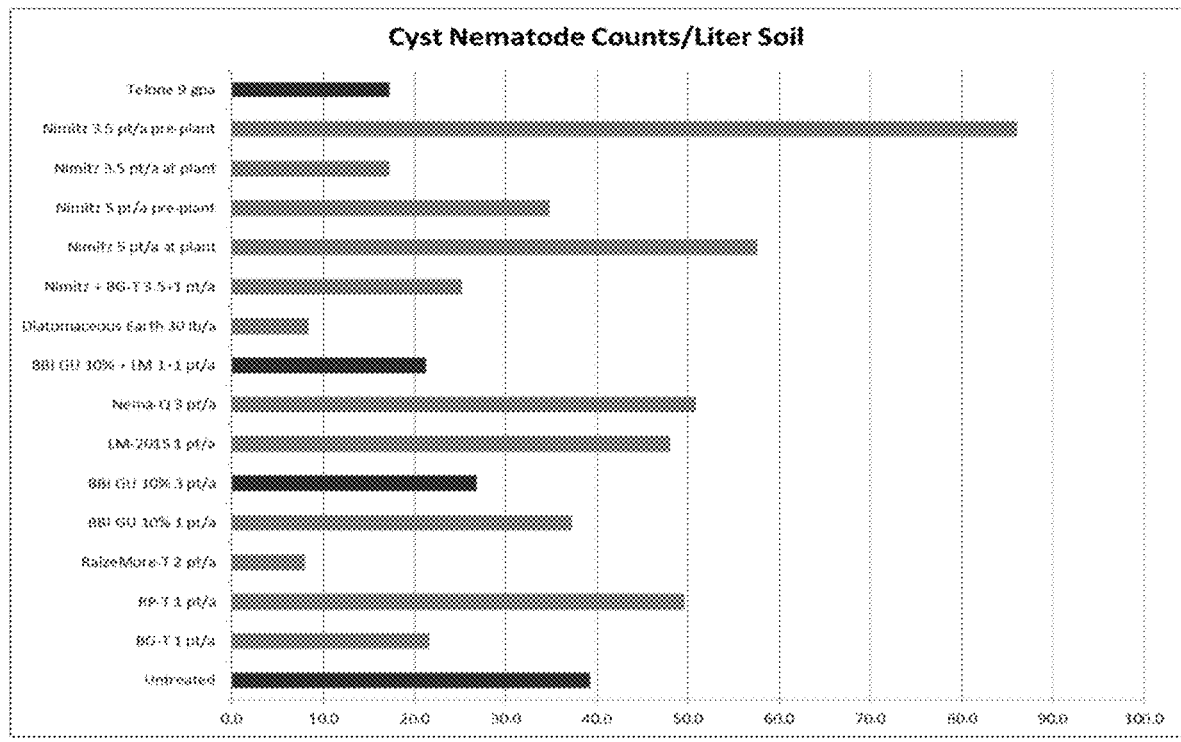
FIG. 5 shows a decrease in cyst nematodes.

In combination with the new wetting agent (LM 2015), there was a marked increase in yield even with GU 10% @ only 1 pt/Acre. The combination of ISO EXTRACT GU 10% @ a 1 pt/Acre+the wetting agent was comparable to GU 10% @ 3 pts/Acre for reducing Cyst Nematode and increasing yield. See also FIGS. 3, 4, and 5.

Example 7—Guayule Root Extract for the Control of Root Knot Nematode (*Meloidogyne javanica*)

The Root Knot nematode is enhanced to grow during the mild winter on a susceptible crop to keep an artificially high level of eggs and juvenile larvae for testing.
Type: Nematode Control
Location: Irvine
Crop: Carrot
Variety: Imperator
Plot Design: Randomized Block
Plot Size: 20'×2.5'
Replicates: 5
Soil Type: Sandy Loam
Irrigation Method: Drip Irrigation
Major Event Dates:

| Pre Application | June 4$^{th}$ | (Telone II injection) |
|---|---|---|
| Planting | July 20$^{th}$ | (Seeds Planted) |
| First Application | June 17$^{th}$ & 18$^{th}$ | (First Soil Application) |
| Second Application | July 1$^{st}$ & 2$^{nd}$ | (Second Soil Application) |
| Third Application | July 14$^{th}$ | (Third Soil Application) |
| Crop Harvest | November 12$^{th}$ | (Harvest) |

Application Information:

| 1) | Untreated Check UTC |
|---|---|
| 2) | BG-T |
| 3) | RP-T |
| 4) | RaizeMore-T |
| 5) | BASC-15-10 |
| 6) | LM-2015 |
| 7) | Nema-Q |
| 8) | Diatomaceous Earth |
| 9) | Nimitz EC |
| 10) | Telone II (See Tables for rates) |

Harvest Date: November 12$^{th}$
Evaluation Methods: At harvest, three feet (0.91 meter) of row from each replicate was harvested and graded into 4 categories: 1) marketable without nematode damage, 2) marketable with nematode damage, 3) not marketable with nematode damage, and 4) not marketable without nematode damage. First sample taken at untreated preplant to establish presence of population. All replicates sampled at harvest, 12, 1 inch (2.5 cm) diameter cores per replicate to a 12 inch (30 cm) depth.
Statistical Analysis: Analysis of Variance (ANOVA) followed by Fisher's Least Significant Difference Test.
Results:

TABLE 5

Figure 6:
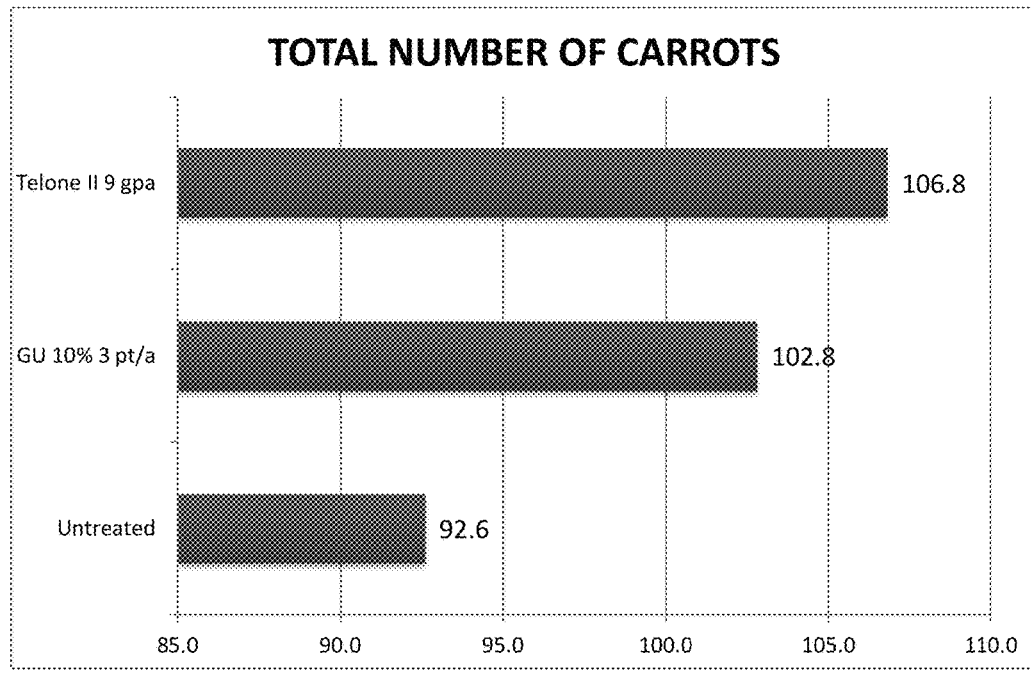
FIG. 6 shows increase in carrot yield.

Harvest data for the Carrot trial
Table 5. Numerically compared to Untreated, *BASC-15-10 at 3 pt/a,
LM-2015, and Telone had a greater Total Number and Weight of carrots.
BG-T and Nimitz + BG-T had a greater Number of carrots than Untreated.
BASC-15-10&LM had a greater Weight of carrots. At P = 0.05, Telone
had a greater Weight of carrots. See also FIG. 6.

|   |   | Total Carrots | | | | |
|---|---|---|---|---|---|---|
|   |   | Number | | Weight (Kg) | | |
|   | Treatment |   | 0.05 | 0.1 | 0.05 | 0.1 |
| 1 | Untreated | 92.60 | AB | ABC | 3.83 | B | B |
| 2 | BG-T pt/a | 98.40 | AB | AB | 3.73 | B | B |
| 3 | RP-T 1 pt/a | 85.40 | AB | ABC | 3.68 | B | B |
| 4 | RaizeMore-T 2 pt/a | 84.60 | AB | ABC | 3.59 | B | B |
| 5 | GU 10% 3 pt/a | 81.40 | AB | BC | 3.82 | B | B |
| 6 | GU 10% 3 pt/a | 102.80 | A | AB | 4.04 | AB | AB |
| 7 | LM-2015 1 pt/a | 104.20 | A | AB | 3.89 | B | B |
| 8 | Nema-Q 3 pt/a | 89.20 | AB | ABC | 3.77 | B | B |
| 9 | BASC-15-10&LM 1 + 1 pt/a | 82.40 | AB | ABC | 3.92 | B | B |
| 10 | Diatomaceous Earth 30 lb/a | 70.20 | B | C | 3.77 | B | B |
| 11 | Nimitz + BG-T 3.5 + 1 pt/a | 96.40 | AB | AB | 3.54 | B | B |
| 12 | Telone II 9 gpa | 106.80 | A | A | 4.54 | A | A |

TABLE 6

Figure 7:
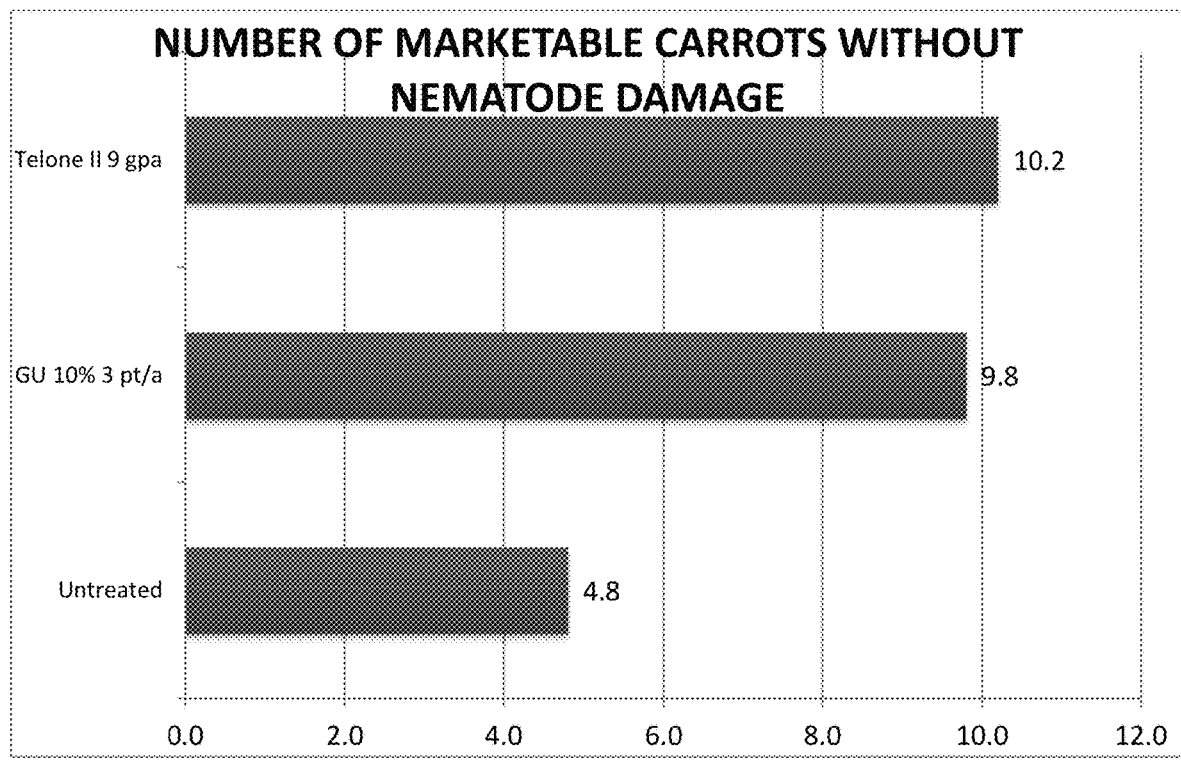
FIG. 7 shows increase in carrot yield.
Figure 8:
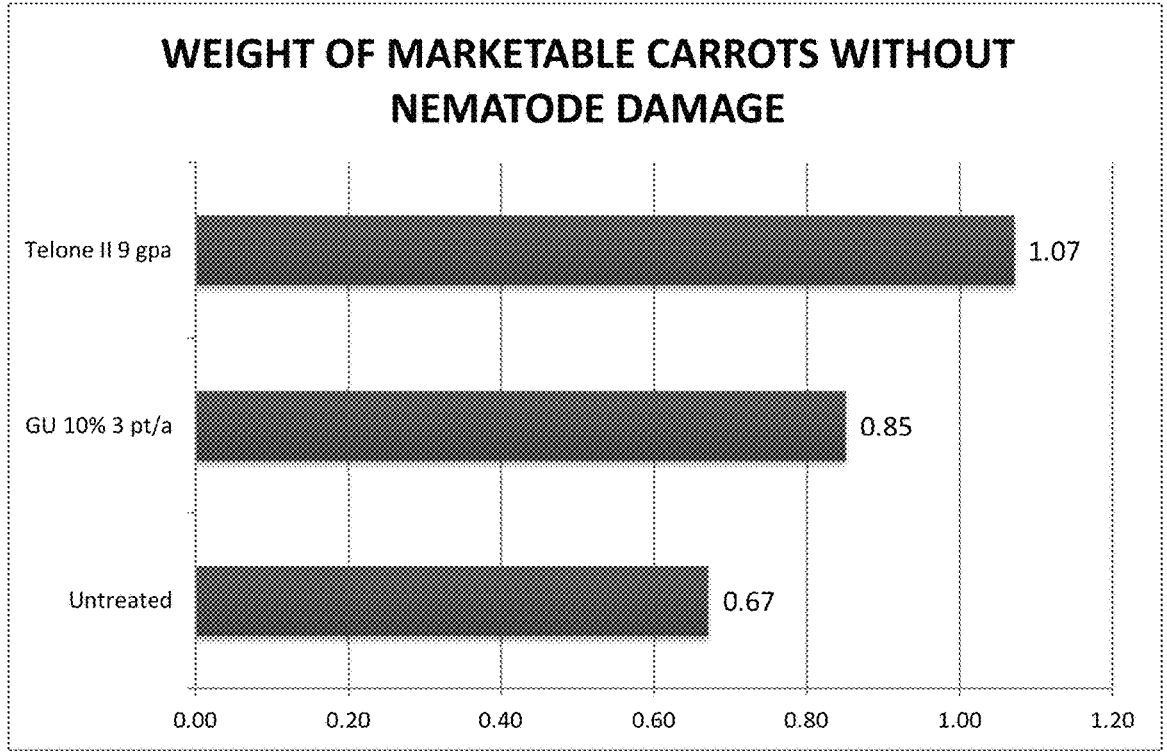
FIG. 8 shows increase in carrot yield.

Further Harvest data for the carrot trial
Table 6. Numerically, BG-T, RP-T, *BASC-15-10 3 pt/ac,
LM-2015, BASC-15-10&LM, Nimitz + BG-T, and Telone had a
greater Number and Weight of Marketable Carrots Without
Nematode Damage than Untreated. RaizeMore-T had a greater
Number of Marketable Carrots Without Nematode Damage than
Untreated. At P = 0.05, Telone had a greater Weight of
Marketable Carrots Without Nematode Damage than Untreated.
See also FIGS. 7 and 8.

|  |  | Marketable Without Nematode Damage | | | | |
| --- | --- | --- | --- | --- | --- | --- |
|  |  | Number | | Weight (Kg) | |
| Treatment |  | 0.05 | 0.1 | 0.05 | 0.1 |
| 1 Untreated | 4.80 | ABC | BCD | 0.67 | BC | BCD |
| 6 GU 10% 3 pt/a | 9.80 | AB | AB | 0.85 | ABC | ABC |
| 12 Telone II 9 gpa | 10.20 | A | AB | 1.07 | A | A |

*BASC-15-10 is code for GU 10% for Carrot Trial

Example—8 Activity Against *Citrus* Nematode

The enzymatic activity against one single molt of *Citrus* nematode *Tylenchulus semipenetrans* placed in sand in a perforated container and placed in soil to determine efficacy of such enzyme on naked proteinaceous skin juvenile nematode stage during a 7 day molting period.

Application Information:
  a.) Iso Extract, 30% 1 ml.+249 mls H2O=250 mls solution.
  b.) Iso Extract 30% 5 ml.+245 mls. H2O=250 mls solution.
  c.) Iso Extract 30% 25 ml.+225 mls. H2O=250 mls solution.
  d.) Untreated H2O=250 mls water only.

Figure 9:
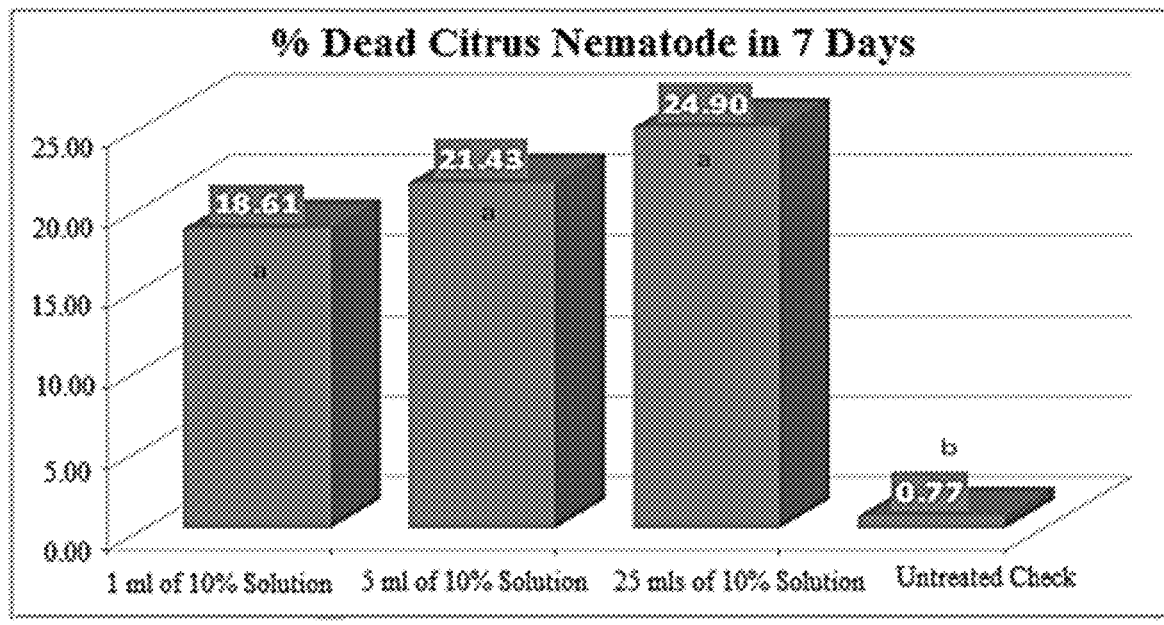
FIG. 9 shows control of citrus nematodes.

Notably all doses were effective and worked well on the portion of population during molt. See FIG. 9.

Example 10—ISO EXTRACT 10% Efficacy on Grape Leafhopper Nymphs and Western Flower *Thrips*

Efficacy was statistically significant for nymphs of Leafhoppers as well as Adults and Nymphs of WF *Thrips*.
  Objective: To determine efficacy of ISO Extract GU 10% on Wine Grape Leafhopper & Western Flower *Thrips*.
  Type: Leafhopper Control
  Location: Lodi, California, USA
  Crop: Wine Grape
  Variety: Old Vine Zinfandel
  Plot Design: Randomized Block
  Plot Size: Three Vines
  Replicates: 6 Replicates per treatment or untreated check, 5×6 Reps=30×3 Vine reps
  Soil Type: Sandy Loam—Hanford Sand Steep
  Soil Notes: 0-2% Slope & >0.1% OM
  Irrigation Method: Drip Irrigation @ 0.5 GPH on 12 hr run cycle
Major Event Dates:

| First Application | Sep 16$^{th}$ | (Foliar Application, one time only) |
| --- | --- | --- |
| First Evaluation | Sep 21$^{th}$ | (Treatments vs Untreated and Grower Standard) |
| First Rainfall | Sept 22rd | (Pests did not return following heavy storm & frost) |

Application Information:

| 1) | Untreated Check UTC |
| --- | --- |
| 2) | Admire Pro @ 1.5 oz/Acre |
| 3) | ISO Extract GU 10% @ 1 pt/Acre (1250 ppm vol./vol) |
| 4) | ISO Extract GU 10% @ 2 pt/Acre (2500 ppm vol./vol) |
| 5) | ISO Extract GU 10% @ 3 pt/Acre (5000 ppm vol./vol) |

Figure 10:
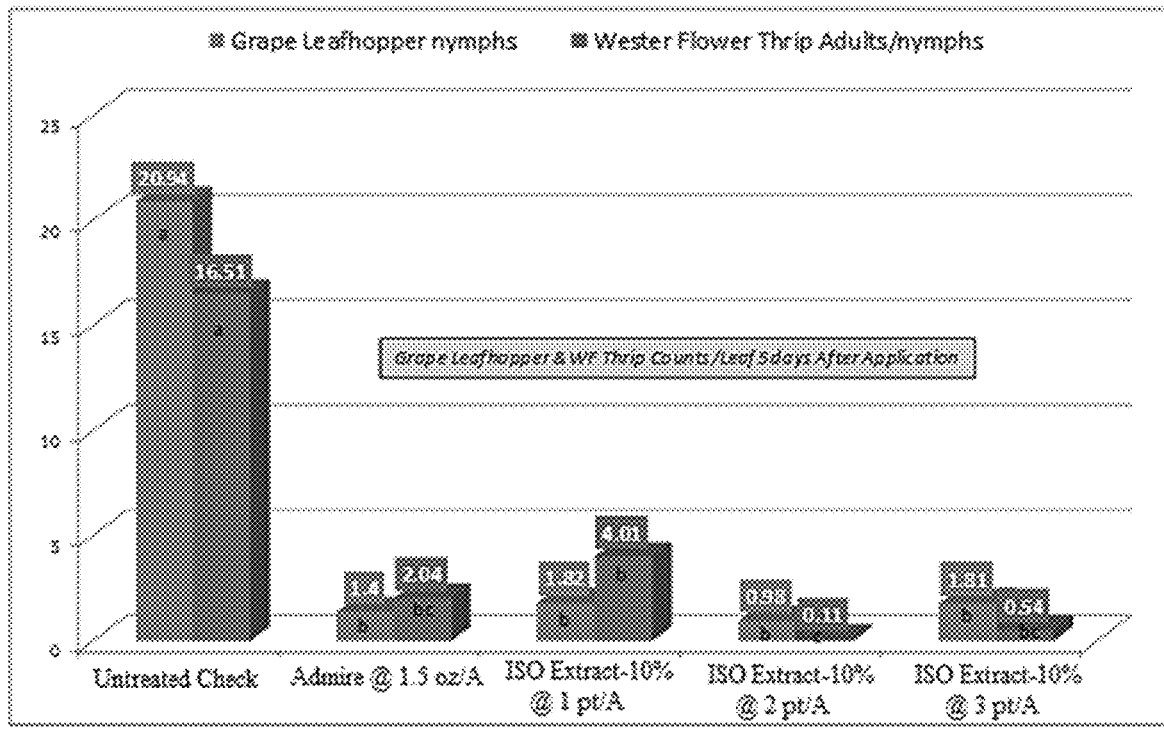
FIG. 10 shows control of grape leafhopper nymphs and western flower thrips.
Figure 11:
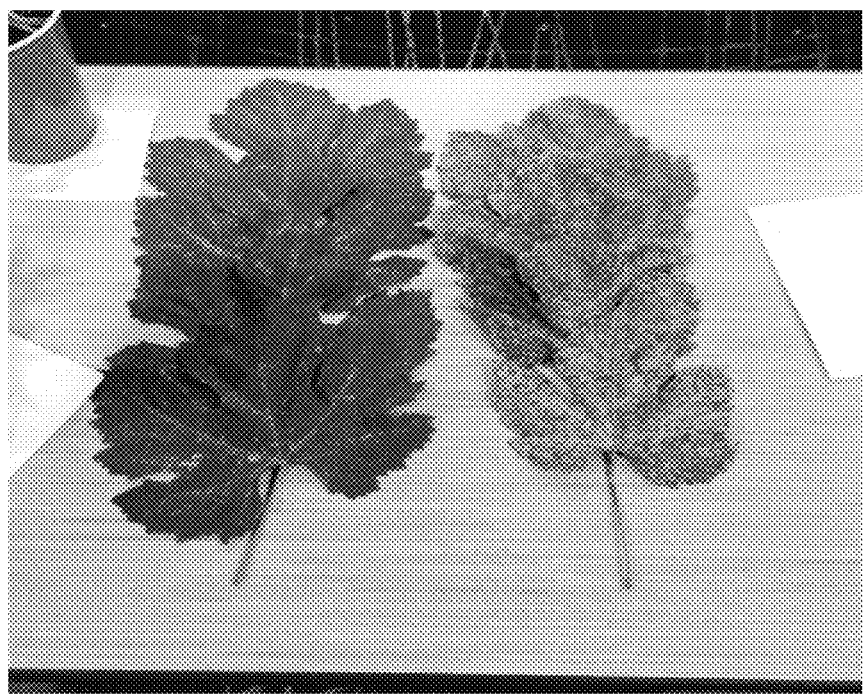
FIG. 11 shows control of grape leafhoppers.

Application Method: Backpack Airblast Sprayer @ 15 liters per treatment calculated to spray 100 GPA
Notes Rate of App: Post-Harvest Application, Grower let the leaf pests go after harvest so Leaf hopper and *Thrips* increase sharply.
Maintenance App: Powdery Mildew Sprays in season, but not after harvest.
Harvest Date: August 26$^{th}$. No pesticides were used 10 days before harvest, or anytime after harvest in this vineyard.
Evaluation Methods: In field visual comparisons were made between the Untreated Check and 4 Treatments to determine overall damage and population density by counting removing 5 leaves per plot/placing in a paper bag and evaluating the leaves within an hour with a dissecting scope. Counts were made of presence of young motile Grape Leafhoppers; adults and young motiles of Western Flower Thrip, too.
Statistical Analysis: ARM Program Version 8.0 (last version Apr. 21, 2013) Duncans' Multiple Range Test, (p=0.05)
Results and Discussion: The active ingredients of this ISO Extract have a dramatic impact, as demonstrated in this trial for knockdown activity, on molting insect pests. See FIGS. 10 and 11.

Grape Leafhopper and Western Flower *Thrips* are two of the most significant pests in grapes annually. The evaluation was done by a researcher of nearly 40 years in Vineyard Management. The ISO extract not only affected the grape insects when molting, but appeared safe to adult foraging bees and wasps. Following a heavy rainfall and frost right after the first evaluation, the product appeared, by the observation of the Researcher, to hold frost injury of the vines for several days or a week long.

Example 10—Effect of Insect Growth Regulation (Enzymatic Effect of Protein Skin of Grape Leafhopper Nymphs)

Objective: To determine efficacy of ISO Extract GQB 23% on Wine Grape
Leafhopper & other soft bodied pests.
Type: Leafhopper Control
Crop: Wine Grape
Variety: Syrah
Plot Design: Randomized Block
Plot Size: 12'×2.5',
Replicates: 8 Replicated Single Grape Vines per treatment or untreated check
Soil Type: Silty Loam
Soil Notes: Soil was moderately moist, but drier than normal.
Irrigation Method: Drip Irrigation Major Event Dates:

| First Application | Jul 25th | (Foliar Application) |
| First Evaluation | Aug 18th | (Leave samples collected, live counts taken) |

Application Information:
1.) Untreated Check UTC
2.) BBI ISO Extract GQB 23% @ 1 pt/Acre Application Method: Handheld pressurized sprayer Notes Rate of App: Hollow Cone Adjustable Nozzle Tip. Sprayed to Runoff on both sides of the leaves.

Evaluation Methods: Leaf samples were collected and bagged 21 days after application to prevent escape of live Leafhoppers. Leaves were observed under a zoom microscope and a total count of live and dead Leafhoppers was taken.

Application Notes: It should be noted that coverage of the entire leaf is preferred to get the best effect from contact with the pests. Leafhopper nymphs and WF Adult Thrip and nymphs spend most of their time on the underside of the leaves.

Statistical Analysis: ARM Program Version 8.0 (last version Apr. 21, 2013) Duncans' Multiple Range Test (P=0.05)

Results: EXTRACT GQB 23% is a blend of three synergistic Plant Based Extracts. Specifically GQB is formulation of Guayule 10%, *Quillaja* 10% and Brassinole 3%.

The application of this product not only had a 3 week residual for control of Grape Leafhopper, but also was non-harmful to eggs of the beneficial predator Green Lacewing.

Additional effects included dramatic reduction in Grape leafhopper leaf damage from the pests sucking mouth parts, with only one application. Also a consistently larger girth of the canes, greener leaves and elongation of the Grape canes.

Figure 12:
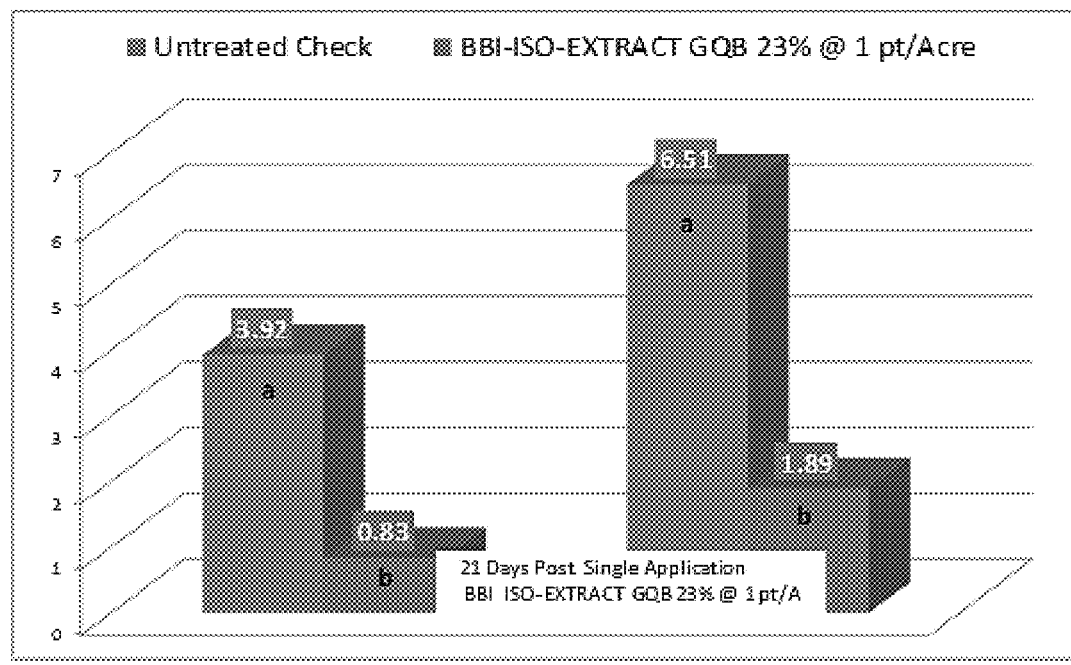
FIG. 12 shows insect growth regulating effect on grape leafhoppers.
Figure 13:
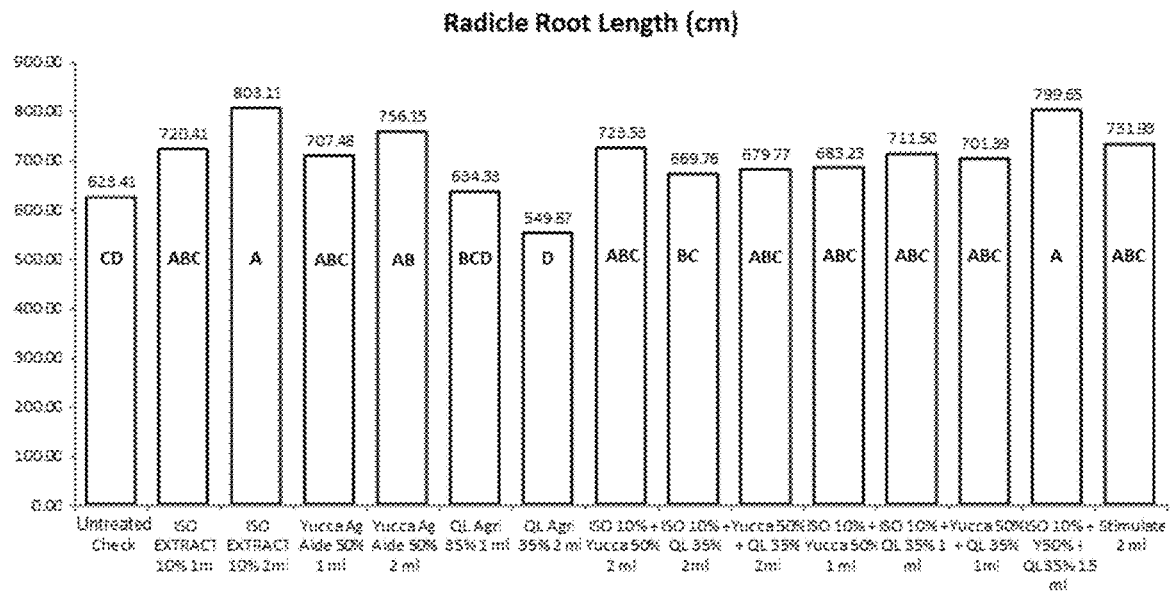
FIG. 13 shows effects on radicle root length.
Figure 14:
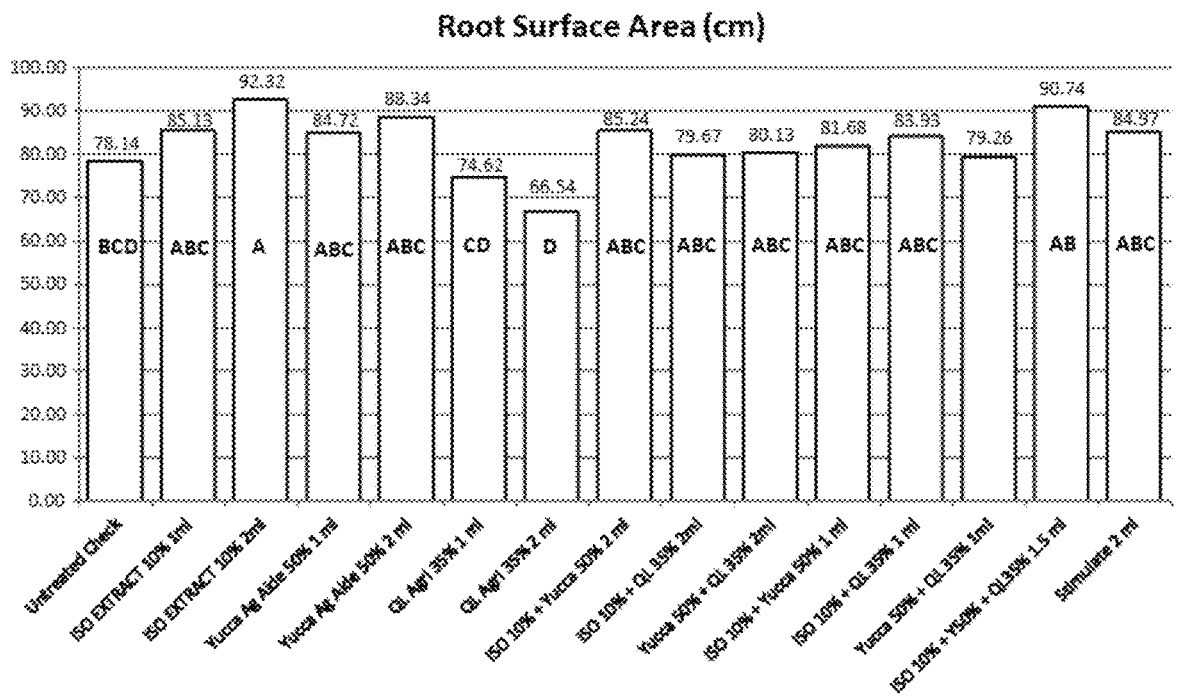
FIG. 14 shows effects on root surface area.
Figure 15:
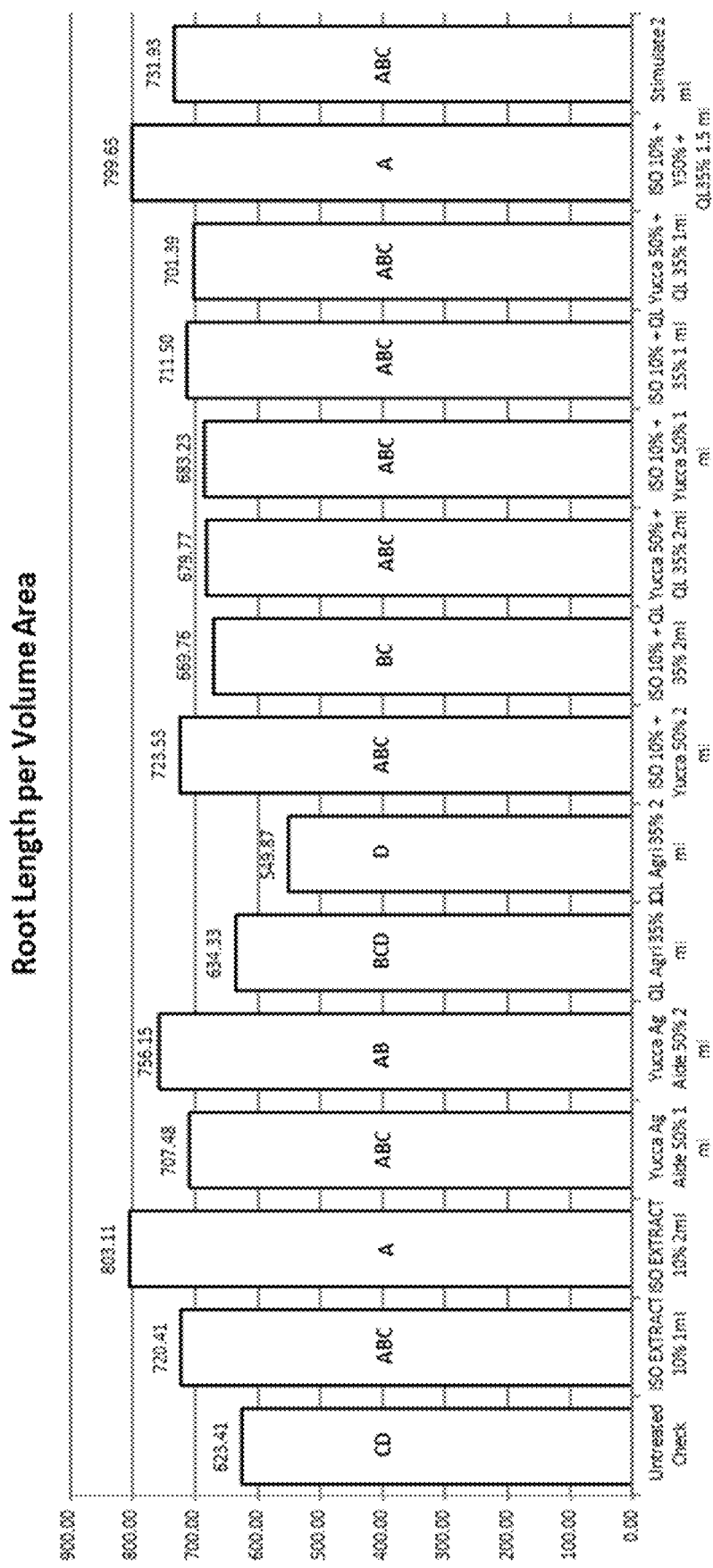
FIG. 15 shows effects on root length.
Figure 16:
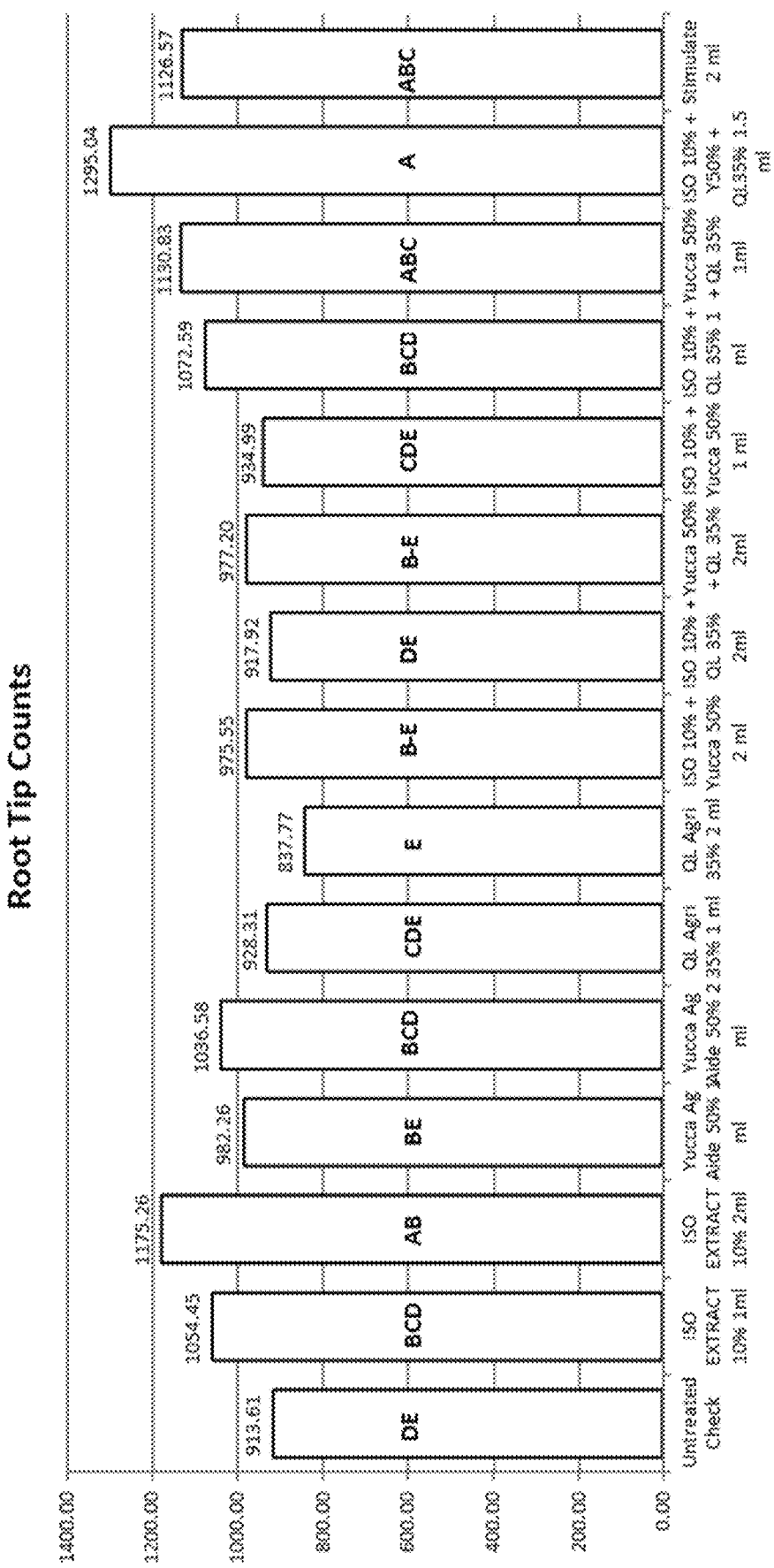
FIG. 16 shows effects on root tip counts.
Figure 17:
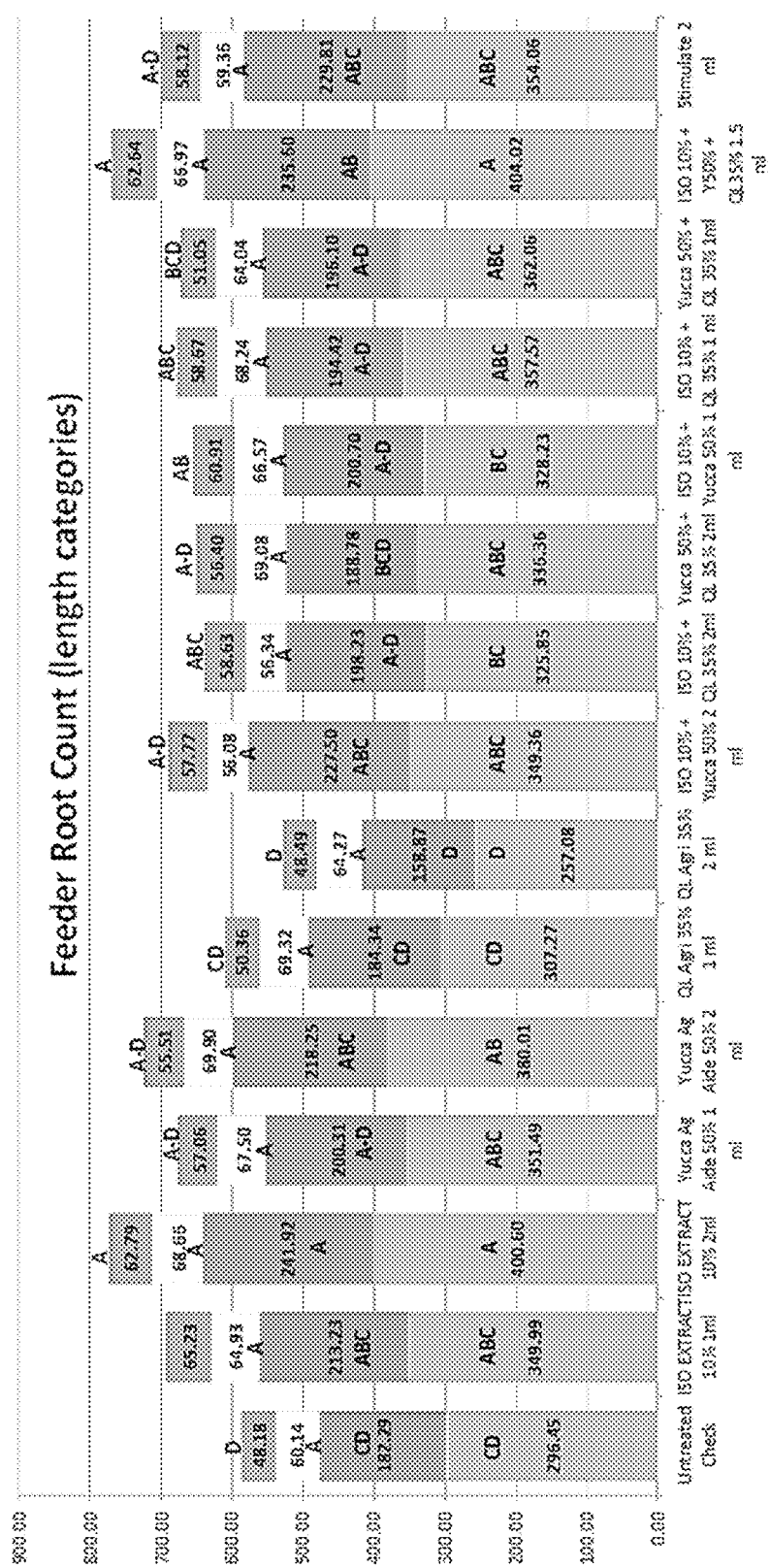
FIG. 17 shows effects on feeder root count.

See FIG. 12

Example 11—Biostimulate/Plant Hormone Effect Related to Active Ingredients from the Root of Guayule Plant Applied as a Soil Drench in Greenhouse Pots with Planted Field Corn Seed ISO EXTRACT 10% (Guayule Root Extract 10%) increased shoot lengths, root lengths, root surface area, and lateral root tips.

Objective: To determine the effects of the extracts on field corn

Type: PGR Study

Crop: Hybrid Field Corn

Variety: 32B10

Plot Design: Randomized Block

Plot Size: 8" Black Plastic Pot

Replicates: 12 for 15 Treatments and Untreated Check

Soil Type: Medium-Fine grain Sand & Potting Mix

Soil Notes:

Irrigation Method: Hand watered using a watering can or sprinkler head hose attachment Major Event Dates:

| First Application | 3/7 | (Solutions applied with mist) |
| Planting Date | 3/7 | (¼"-½" planting depth in sand) |
| First Evaluation | 3/21 | (Reps pulled and evaluated) |

Application Information:
1) Untreated Check (water check only)
2) ISO EXTRACT 10% 1 ml
3) ISO EXTRACT 10% 2 ml
4) *Yucca* Ag Aide 50% 1 ml
5) *Yucca* Ag Aide 50% 2 ml
6) QL Agri 35% 1 ml
7) QL Agri 35% 2 ml
8) ISO 10%+*Yucca* 50% 1 ml
9) ISO 10%+QL 35% 1 ml
10) *Yucca* 50%+QL 35% 1 ml
11) ISO 10%+*Yucca* 50% 2 ml
12) ISO 10%+QL 35% 2 ml
13) *Yucca* 50%+QL 35% 2 ml
14) ISO 10%+Y50%+QL35% 1.5 ml
15) Stimulate 2 ml Application Method: Applied by syringe over top of soil as 10 mls of solution per rep Harvest Date: 3/21

Evaluation Methods: Shoot and Root measurements taken with straight ruler using centimeter increments. Shoot evaluated for total length from seed to tip. Roots evaluated as Radicle, Seminal, and Nodal for both length in centimeters and count for Nodal roots.

Statistical Analysis: ARM Program Version 8.0 (last version Apr. 21, 2013) Duncans' Multiple Range Test The results were favorable as can be seen in FIGS. 13-17.

Example 12—ISO Extract 10% (Guayule Root Extract 10%) Applied as a Soil Drench Over Planted Cotton Seed in Greenhouse Trial Objective: Plant and root growth Type: BioStimulant PGR Trial Crop: Cotton Variety: DP1216B2RF Plot Design: 12 treatments & an Untreated Check, 12 reps/treatment Plot Size: greenhouse 18 oz. plots Replicates: 12 Replicates per treatment Soil Type: Sand Soil Notes:

Irrigation Method: Micro sprinkler Irrigation

Major Event Dates:

| Planting date | 4/28 | (Planted in greenhouse 18" pots) |
| Treatment date | 5/4 | (10 mls. of solution) |
| First evaluation | 5/18 | (Root, shoot measurements, dry matter, percent moisture) |
| Second evaluation | 6/10 | (Root, shoot measurements, dry matter, percent moisture) |

Application Information:

| 1) | Untreated Check | UTC |
| 2) | ISO Extract 10% | 1000 PPM |
| 3) | ISO Extract 10% | 2000 PPM |

| | | |
|---|---|---|
| 4) | ISO Extract 10% | 3000 PPM |
| 5) | Yucca 50% | 1000 PPM |
| 6) | Yucca 50% | 2000 PPM |
| 7) | Yucca 50% | 3000 PPM |
| 8) | Quillaya | 1000 PPM |
| 9) | Quillaya | 2000 PPM |
| 10) | Quillaya | 3000 PPM |
| 11) | ISO10% + Yucca | 1000 + 1000 PPM |
| 12) | ISO10% + Quillaya | 1000 + 1000 PPM |
| 13) | Yucca + Quillaya | 1000 + 1000 PPM |

Figure 18:
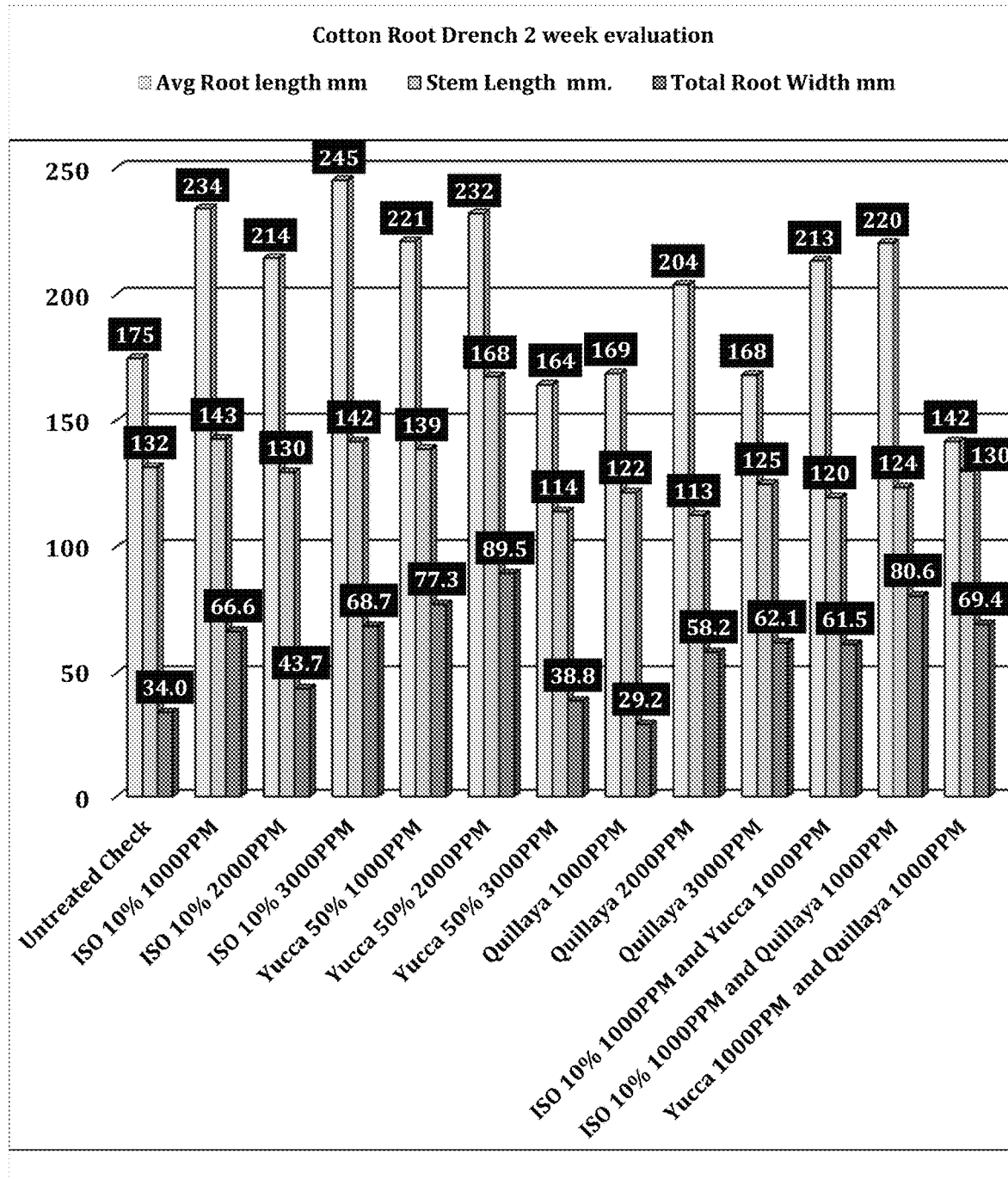
FIG. 18 shows effects on roots and stems.
Figure 19:
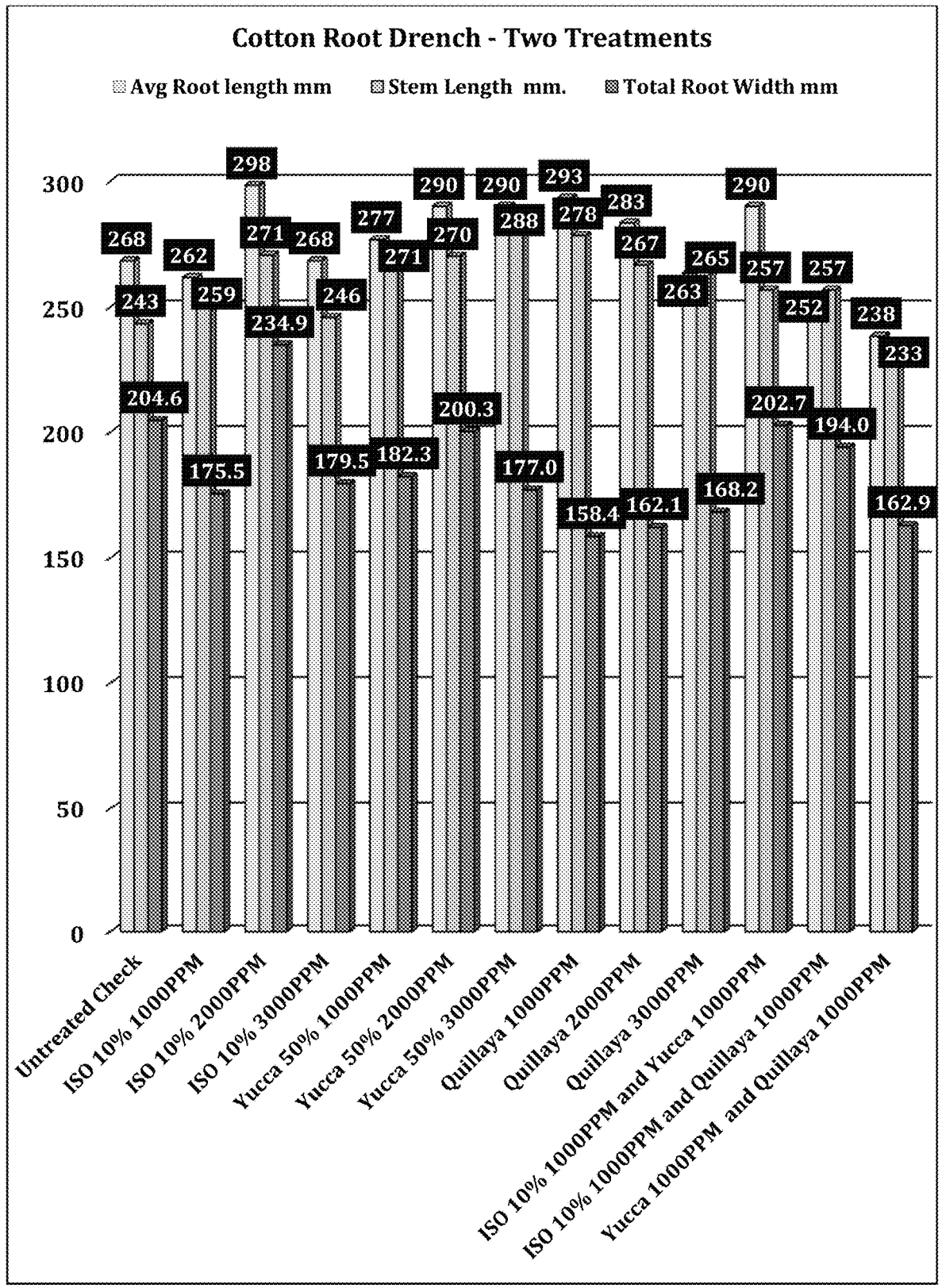
FIG. 19 shows effects on roots and stems.
Figure 20:
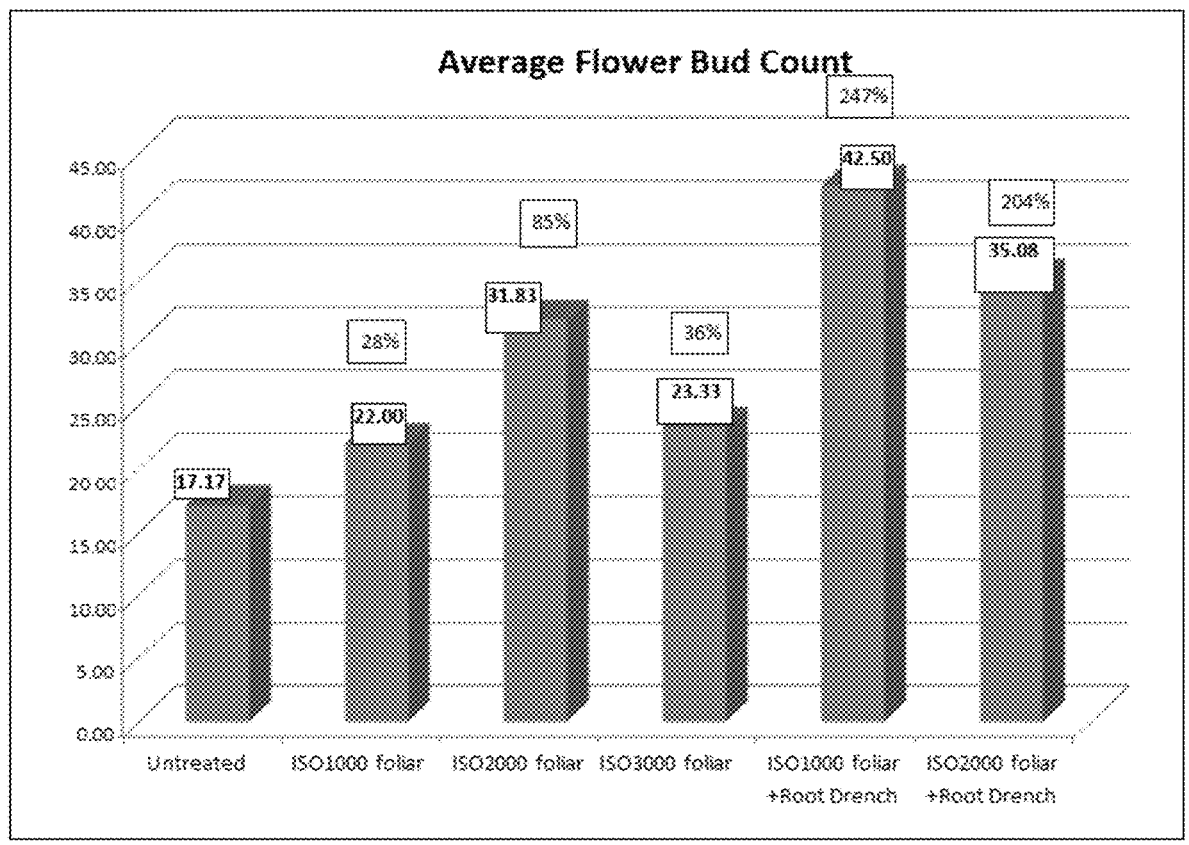
FIG. 20 shows effects on flower bud count.
Figure 21:
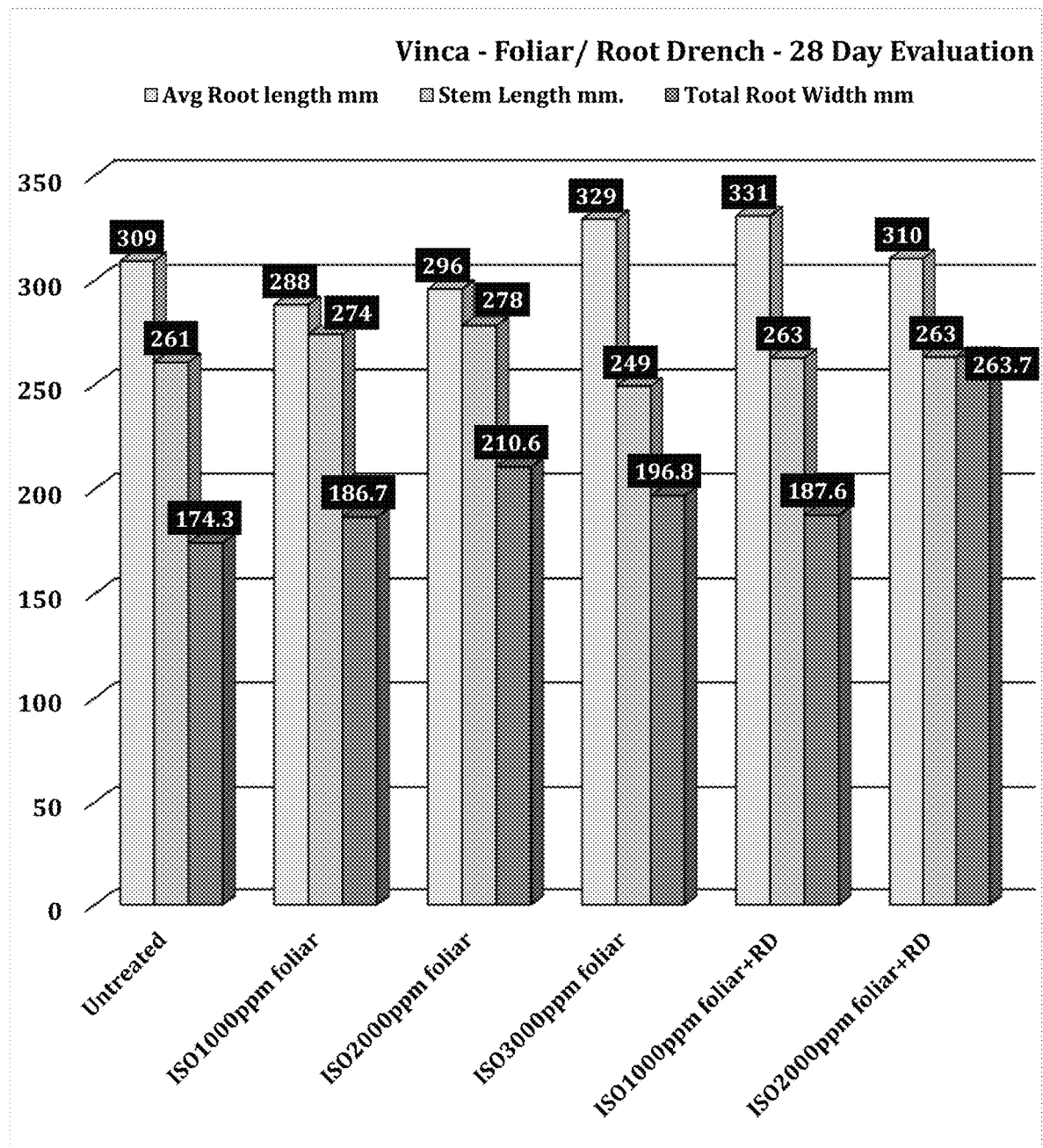
FIG. 21 shows effects on roots and stems.
Figure 22:
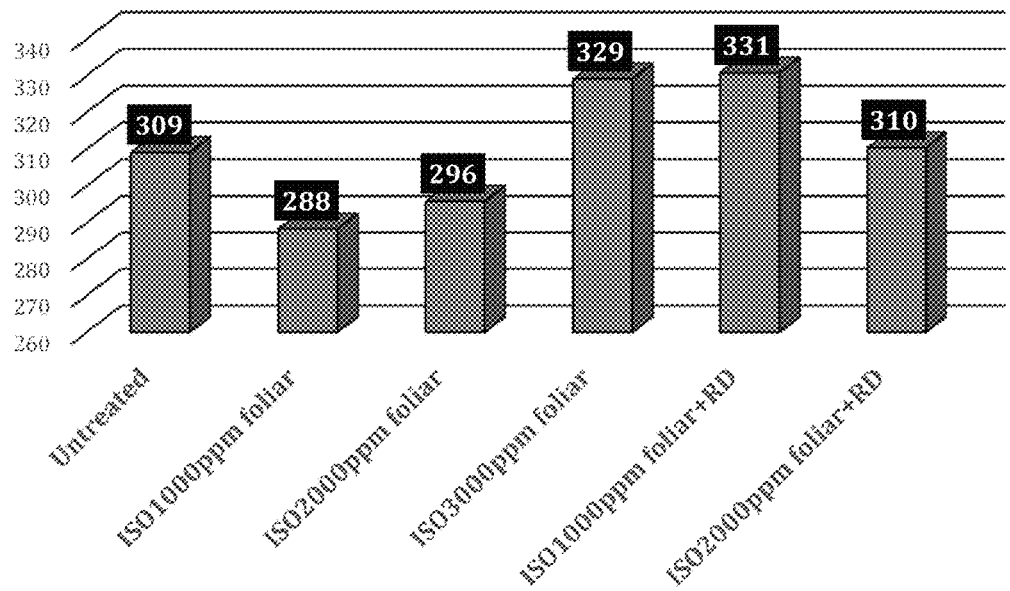
FIG. 22 shows effects on root length.
Figure 23:
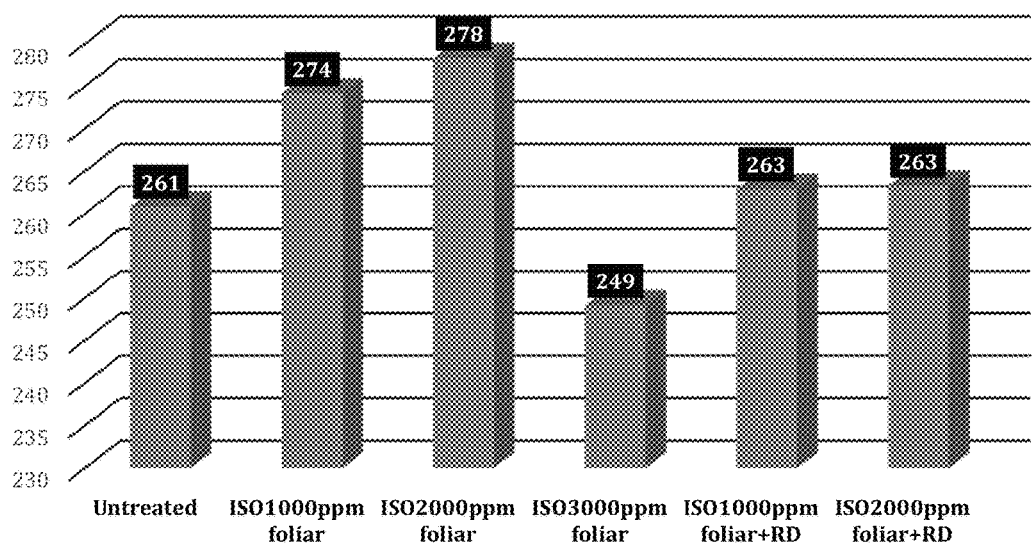
FIG. 23 shows effects on stem length.

Application Method: Applied as a drench 10 mls per treatment.
Evaluation Date: Seven days after treatment and 14 days after treatment
Evaluation Methods: Planted into sand, 18 ounce pots. Sand was the growing media with a half inch soil for seed germination. Irrigation was applied through micro sprinklers 14 GPH for a total of 5 minutes per day. The first evaluation took place fourteen days after treatment and the second evaluation took place 21 days after treatment. Plant nutrition—liquid 12-4-8, 20 mls/week (sand media)
Statistical Analysis: ARM Program Version 8.0 (last version Apr. 21, 2013) Duncans' Multiple Range Test
The favorable results can be seen in FIGS. 18 and 19.

Example 13—Trial was Conducted as a Foliar Rather than Seed Treatment or Soil Drench Application in a Greenhouse Setting Objective: Blooms/buds, plant and root growth
Crop: Commercial *Vinca*
Variety: Hybrid
Plot Design: 5 treatments & an Untreated Check Total 6 treatments
Plot Size: greenhouse 1 gallon plots
Replicates: 12 Replicates per treatment
Soil Type: Sand
Irrigation Method: Micro sprinkler Irrigation 14 GPH
Major Event Dates:

| | |
|---|---|
| Transplant Date | 7/1 |
| First treatment | 7/5 |
| Second treatment | 7/12 |
| Evaluation date | 7/28 |
| First evaluation | 7/28 |

Application Information:

| | | | |
|---|---|---|---|
| 1) | Untreated Check | UTC | |
| 2) | ISO Extract 10% | 1000 Foliar | PPM |
| 3) | ISO Extract 10% | 2000 Foliar | PPM |
| 4) | ISO Extract 10% | 3000 Foliar | PPM |
| 5) | ISO Extract 10% | 1000 Foliar + | PPM |
| | | 1000 RootApp | PPM |
| 6) | ISO Extract 10% | 2000 Foliar + | PPM |
| | | 2000 RootApp | PPM |

Application Method: Applied as a Foliar spray Treatments 1-4. Treatments 5 and 6 Foliar spray plus Root drench, treatments, 10 mls per plant of these two treatments.
Evaluation Methods: Transplanted into sand, 1 gallon pots. Sand was the growing media with a 0.24 of soil for seed germination. Irrigation was applied through micro sprinklers 14 GPH for a total of 5 minutes per day. The first evaluation took place fourteen days after treatment and the second evaluation took place 21 days after treatment. Plant nutrition—liquid 12-4-8, 20 mls/week (sand media)
Application Notes: Foliar Spray treatment/Root Drench *Vinca*
Statistical Analysis: ARM Program Version 8.0 (last version Apr. 21, 2013) Duncans' Multiple Range Test
Summary and Discussion:

Seed treatment rates of ISO EXTRACT 10% can be done at, for example, 0.5 oz, 1 oz, 2 oz, or 3 oz/100 lbs of seed. Drench treatments can be done at, for example, 1, 2 or 3 mls of ISO EXTRACT 10% over the planted seed or, in the case of peppers and tomatoes, drench on the roots. Significant increases in root development and shoot development, as well as fresh and dry weight or roots, shoots and or whole plants have occurred. *Vinca* plants were treated with a foliar treatment of 1, 2 or 3 mls/Liter of water (1000, 2000 or 3000 ppm vol/vol. solution). Foliar and soil applications were done at the same time on two treatments. Plant hormone and sugar pathways are different in the root system and in the upper part of the plant. More auxins in the top and more cytokinins in the roots as a simple example of hormone differences, as well as movement of sugars during vegetative stages vs when the fruit sinks are growing in the top part of the plant. On the *Vinca* the combination of 1000 ppm applied twice to the tops and 1000 ppm applied twice to the roots on the same days (1$^{st}$ day and 2 weeks later), then evaluated once 2 weeks after the second application. This tells us something about potential use of the product in the field for fruiting vegetables and trees, soybean pods, corn kernels and ornamental plants that flower. Where we did 1000, 2000 or 3000 ppm applications foliar twice, the classic dose response of a typical Plant Growth Regulator or BioStimulant was achieved, e.g., increase in flowers was 28%, 85% and 36% showing the typical increase than decrease but still better than untreated. This is known as the triple effect. Coupling this response with soil applications, which increase the effectiveness of the roots system at the same time as tops achieves 200%+when soil and top applications are combined. Rates can be reduced if desired when treating soil and tops combined.

The favorable results can be seen in FIGS. 20-23

Example 14—Foliar Application of Commercial Sweet Corn Replicated Trials

The trial demonstrated the potential with proper timing on Corn plant at V-3, V-5 & Tassel to increase yield and size of kernels without loss of corn cobb size.

Objective: Determine the impact of 1 & 2 pts/Acre applications in season on Sweet Corn
Type: Plant BioStimulant/Plant Growth Regulator (Sweet Corn Production)
Crop: Sweet Corn
Variety: 3674
Plot Design: Randomized Block
Plot Size: 30'×66'
Replicates: 6
Soil Notes: Soil Moisture was good throughout growing season
Irrigation Method: Furrow/Surface Irrigation Major Event Dates:

| Planting | Jul 25th | |
|---|---|---|
| First Application | Aug 25th | (Foliar Application at V-3) |
| Second Application | Sep 10th | (Foliar Application at Pre-Tassle) |
| Third Application | Sep 17th | (Foliar Application at Early Silk) |
| Harvest Date | Oct. 10th | (Mature Sweet Corn Harvest) |

Application Information:

| 1) | Untreated Check | UTC | | |
|---|---|---|---|---|
| 2) | BBI ISO EXTRACT | GU 10% | 1 pt/Acre | 40 Gallons Water |
| 3) | BBI ISO EXTRACT | GU 10% | 2 pt/Acre | 40 Gallons Water |

Application Method: C02 Backpack Sprayer @ 40 psi calculated to spray 40 Gallons per Acre.
Notes Rate of Appl: No adverse effects (phytotoxic) noted from applications of ISO EXTRACT GU 10%
Harvest Date: October 10
Evaluation Methods: Hand Harvested Total Plot Area, Measurement Girth, Length and Individual Weight of Ears
Statistical Analysis: ARM Program Version 8.0 (last version Apr. 21, 2013) Duncans' Multiple Range Test
Results & Discussion Trial was conducted in the Northern San Joaquin Valley Sweet Corn growing region of California. ISO EXTRACT GU 10% was effective at increasing both total yield and Girth of the Ears of Corn, which increased the weight in addition to more ears per plot. The application timing was convenient and fit in with cultural practices with sprays for herbicides and insecticides & miticides.

The fact there was and increase for both rates and yet not significantly higher with the 2 pt rate, confirms earlier research where the dose response for the ISO EXTRACT GU 10% was effective at 8 oz –2 pts/Acre but not at higher rates. This is the typical Plant Growth Hormone effect when exogenous applications of Plant Growth Regulators are applied there is what is known as the "Triple effect". This starts with dose response increase, then a leveling off of the effect (such as plant height, fruit size, root length) and then finally a reverse. The yield increase over 15% over the untreated check is considered quite good for increase in Sweet Corn production per acre.

Figure 24:
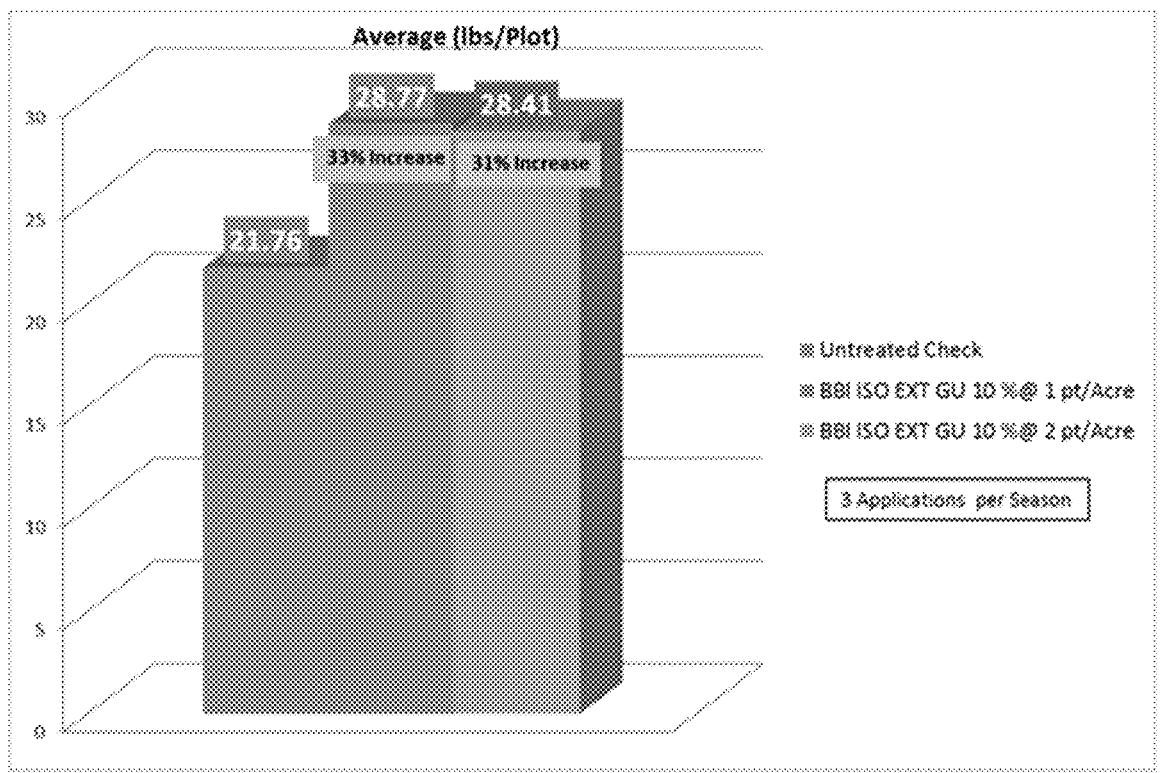
FIG. 24 shows effects on yield.
Figure 25:
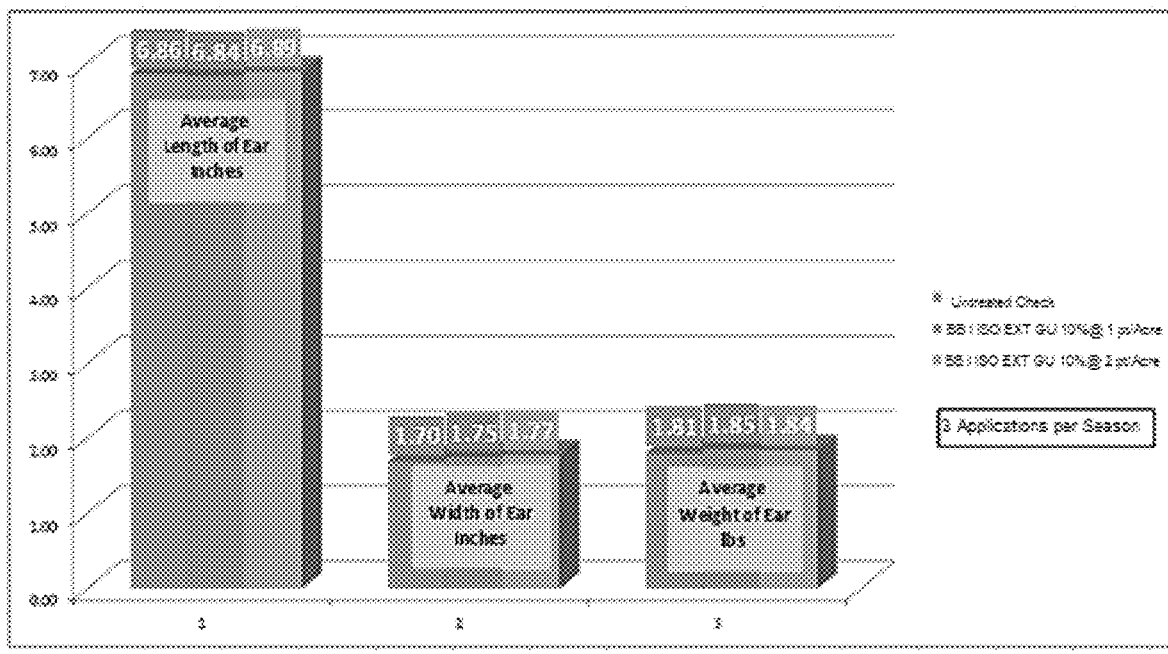
FIG. 25 shows effects on corn ear size.

Advantageously, these aforementioned components are naturally derived from one or more plants and together serve to regulate the target plant's growth and defense mechanism, improve the plant's anti-oxidative effects, and control the transportation of plant hormones. See FIGS. 24 and 25

All patents, patent applications, provisional applications, and publications referred to or cited herein are incorporated by reference in their entirety, including all figures and tables, to the extent they are not inconsistent with the explicit teachings of this specification.

It should be understood that the examples and embodiments described herein are for illustrative purposes only and that various modifications or changes in light thereof will be suggested to persons skilled in the art and are to be included within the spirit and purview of this application.

REFERENCES

Abbott, Derek A., de Hulster, Erik, Duong, Giang-Huong, Pronk, Jack T., Suir, Erwin, and van Maris, Antonius J. A. Catalase Overexpression Reduces Lactic Acid-Induced Oxidative Stress in *Saccharomyces cerevisiae Appl. Environ Microbiol* 2009 Apr. 27; 75(8):2320-5. Epub 2009 Feb. 27.

Abea, Hiroshi, Dubouzeta, Joseph G., Liua, Qiang, Sakumaa, Yoh, Shinozakid, Kazuo, and Yamaguchi-Shinozakia, Kazuko, DNA-Binding Specificity of the ERF/AP2 Domain of *Arabidopsis* DREBs, Transcription Factors Involved in Dehydration- and Cold-Inducible Gene Expression *Biochemical and Biophysical Research Communications* Volume 290, Issue 3, 25 Jan. 2002, Pages 998-1009

Alet, Analía I, Altabella, Teresa, Carrasco, Pedro, Cuevas, Juan C., del Valle, Secundino, Espasandin, Fabiana D., Ferrando, Alejandro, González, María E., Marco, Francisco, Ruiz, Oscar A., Sanchez, Diego H., and Tiburcio, Antonio, F., *Putrescine accumulation in *Arabidopsis thaliana* transgenic lines enhances tolerance to dehydration and freezing stress *Plant Signal Behav.* 2011 February; 6(2):278-86. Epub 2011 Feb. 1

Allegro, Gianni, Balestrazzi, Alma, Belenghi, Beatrice, Calligari, Paolo, Confalonieri, Massimo, Delledonne, Massimo, Levine, Alex, Picco, Franco, and Zelasco, Samantha. Transformation of white poplar (*Populus alba* L.) with a novel *Arabidopsis thaliana* cysteine proteinase inhibitor and analysis of insect pest resistance. Molecular Breeding January 2001, Volume 7, Issue 1, pp 35-42

Altabella, Teresa, Gallart, Marta, Planas-Portell, Joan, and Tiburcio, Antonio F.; BMC Plant Biology 201313:109; DOI: 10.1186/1471-2229-13-109© Planas-Portell et al.; licensee BioMed Central Ltd. 2013, Received: 4 Mar. 2013Accepted: 30 Jul. 2013Published: 5 Aug. 2013, Copper-containing amine oxidases contribute to terminal polyamine oxidation in peroxisomes and apoplast of *Arabidopsis thaliana*

Amachi, Teruo, Hirakawa, Shuji, Kuroda, Kouichi, Ogasa Tatsuya Uraji, Kazuo, Shinji, Kazunori, Suzuki, Masayuki, and Ueda, Mitsuyoshi, Growth acceleration of plants and mushroom by erythritol *Plant Biotechnology* 25, 489-492 (2008)

Araujo, Wagner L., Fernie, Alisdair R., Gaertner, Stefanie, Horst, Ina, Kebeish, Rashad, Klaus, Stephanie, Krause, Katrin, Niessen, Markus, Peterhansel, Christoph, and Staebler, Norma. Two alanine aminotranferases link mitochondrial glycolate oxidation to the major photorespiratory pathway in *Arabidopsis* and rice. *Journal of Experimental Botany*, Page 1 of 12 doi:10.1093/jxb/err453

Ashrafa, M. and Fooladb, M. R. Roles of glycine betaine and proline in improving plant abiotic stress resistance. *Environmental and Experimental Botany* Vol 59, Issue 2, March 2007, Pages 206-216

Azevedo, R. A., Lancien, M., and P. J. Lea. The aspartic acid metabolic pathway, an exciting and essential pathway in plants. Amino Acids. 2006 March; 30(2):143-62. Epub 2006 Mar. 10

Bachhawat, Anand K. and Kumarl, Akhilesh, Pyroglutamic acid: throwing light on a lightly studied metabolite. *Current Science* (Ser. No. 00/113,891); Jan. 25, 2012, Vol. 102 Issue 2, p 288

Bai, Linquan, Kang, Qianjin, Lu, Yuzhen, Wang, Bing, and Wanga, Chengshu, Unveiling the biosynthetic puzzle of destruxins in Metarhizium species. *Proceedings of the National Academy of Sciences* 109(4):1287-92 • January 2012

Bailey-Serres, Julia, Branco-Price, Cristina, Jang, Charles J. H., Kaiser, Kayla A., and Larive, Cynthia K., Selective mRNA translation coordinates energetic and metabolic adjustments to cellular oxygen deprivation and reoxygenation in *Arabidopsis thaliana. The Plant Journal* (2008) 56, 743-755

Bak, Søren, Fürstenberg-Hägg, Joel, and Zagrobelny, MikaPlant Defense against Insect Herbivores. *Int. J. Mol. Sci.* 2013, 14(5), 10242-10297; doi:10.3390/ijms140510242

Barakatl, Hoda M., El-Tohamy, M. M., Halieml, A. S., Mahfozl, and Hala M. Mahfozl; Detection of Genetic Damage Induced by Plant Growth Hormone Putrescine on *Allium cepa* and *Vicia faba*; Faculty of Sciences, Ain Shams University, Egypt 2. Academy of Scientific Research and Technology grant student, Egypt Barroso, Juan B., Corpas, Francisco J., del Rio, Luis A., and Palma, Jose M., Protein tyrosine nitration in higher plants grown under natural and stress conditions. Front; Plant Sci. 2013 Feb. 25; 4:29. doi: 10.3389/fpls.2013.00029. eCollection 2013

Baudier, Kaitlin M., Diangelus, Katherine L., Kaschock-Marenda, Simon D., Marenda, Daniel R., O'Donnell, Sean, and Patel, Nirali, Erythritol, a Non-Nutritive Sugar Alcohol Sweetener and the Main Component of TruviaH, Is a Palatable Ingested Insecticide PLOS One www.plosone.org June 2014 Volume 9 Issue 6 e98949

Biochemical and Biophysical Research Communications Volume 313, Issue 2, 9 Jan. 2004, Pages 369-375 Branched Chain Amino Acids, *Arabidopsis* stress-inducible gene for arginine decarboxylase AtADC2 is required for accumulation of putrescine in salt tolerance Bohnert H J, Bornhouser A, Ishitani M, Jensen R G, Majumder A L, and Michalowski C B, Coordinate transcriptional induction of myo-inositol metabolism during environmental stress. *Plant J.* 1996 April; 9(4):537-48

Bohnert, Hans J., Jensen, Richard G., and Nelson, Donald E., Adaptations to Environmental Stresses *The Plant Cell, Vol.* 7, 1099-1 111, July 1995 1995 American Society of Plant Physiologists Bonaretti Jay. VALINE FACTS, BENEFITS, USES & FUNCTIONS. *Aminoz.com.au* Apr. 7, 2010

Bourgin, J. P., Goujaud, J., Missonier, C., and Pethe, C., Valine-Resistance, a Potential Marker in Plant Cell Genetics. I. Distinction between Two Types of Valine-Resistant Tobacco Mutants Isolated from Protoplast-Derived Cells. Copyright 0 1985 by the *Genetics Society of America*

Cakmak, Ismail, Hengeler, Christine, and Marschner, Horst. Changes in phloem export of sucrose in leaves in response to phosphorus, potassium and magnesium deficiency in bean plants. *J. Exp. Bot.* (1994) 45 (9): 1251-1257

Campos, Vincent P., Campos, Viviane A. C., Machado, Alan R. T., Oliveira, Denilson F., Silva, Willian R. J., and Zeri, Ana C. M., Volatile organic compounds for the control of *Meloidogyne exigua* in *Coffea Arabica Trop. plant pathol.* vol. 38 no. 5 Brasilia September/October 2013

Chang, Young-Chae, Cho, Gun, Chung, Tae-Wook, Kim, Cheorl-Ho, Kim, Jong-Guk, Kim, Soo-Hyun, Ko, Jeong-Heon, Lee, Young-Choon, and Moon, Sung-Kwon. Novel and therapeutic effect of caffeic acid and caffeic acid phenyl ester on hepatocarcinoma cells: complete regression of hepatoma growth and metastasis by dual mechanism. *FASEB J* November 2004 18:1670-1681

Chinnusamy, Viswanathan and Zhu, Jian-Kang, Epigenetic regulation of stress responses in plants. *Curr Opin Plant Biol.* 2009 April; 12(2):133-9. doi: 10.1016/j.pbi.2008.12.006. Epub 2009 Jan. 27

Christiansen, Nicole, Ehrhardt, Thomas, Grossmann, Klaus, Hutzler, Johannes, Looser, Ralf, and Tresch, Stefan. On the mode of action of the herbicides cinmethylin and 5-benzyloxymethyl-1, 2-isoxazolines: putative inhibitors of plant tyrosine aminotransferase. *Pest Manag Sci.* 2012 March; 68(3):482-92. doi: 10.1002/ps.2319. Epub 2011 Nov. 10 Naohito Aoki, Yumiko Yamaguchi-Aoki and Axel Ullrich The Novel Protein-tyrosine Phosphatase PTP20 Is a Positive Regulator of PC12 Cell Neuronal Differentiation. *J Biol Chem.* 1996 Nov. 15; 271(46):29422-6.

Churchill, Alice C. L., Gibson, Donna M., Giuliano Garisto Donzelli, Bruno, Krasnoff, Stuart B., and Sun-Moon, Yong; Genetic basis of destruxin production in the entomopathogen *Metarhizium robertsii. Current Genet.* 2012 April; 58(2):105-16. doi: 10.1007/s00294-012-0368-4. Epub 2012 Feb. 25

Cruz-Ramirez, Alfredo, Herrera-Estrella, Luis, and Lopez-Bucio, Jose, The role of nutrient availability in regulating root architecture *Curr Opin Plant Biol.* 2003 June; 6(3): 280-7.

Dasha, Saswati, Lee, Hyunjoo, and Oh, Jinho, a Selective conversion of glycerol to 1,3-propanediol using Pt-sulfated zirconia *Green Chem.*, 2011, 13, 2004-2007

Davis, E. L. and Tylka, G. L. Soybean cyst nematode disease. 2000. Soybean cyst nematode disease. The Plant Health Instructor. DOI: 10.1094/PHI-I-S-01. Updated S 200S Dutta Satyajit, Ray Supratim, and Nagarajan K Glutamic acid as anticancer agent: An overview. *Saudi Pharmaceutical Journal* Volume 21, Issue 4, October 2013, Pages 337-343

Fu, Hui-Hua, Gupta, Rajeev, Luan, Sheng, and Xu, Qiang. Molecular Characterization of a Tyrosine-Specific Protein Phosphatase Encoded by a Stress-Responsive Gene in *Arabidopsis. Plant Cell.* 1998 May; 10(5):849-57

Gzik, A. Accumulation of proline and pattern of α-amino acids in sugar beet plants in response to osmotic, water and salt stress. Environmental and Experimental Botany Volume 36, Issue 1, May 1996, Pages 29-38

Hallsworth, John E. and Magan, Naresh, Manipulation of intracellular glycerol and erythritol enhances germination of conidia at low water availability. Microbiology. 1995 May; 141 (Pt 5):1109-15.

Hanson, Andrew D., McNeil, Scott D., and Nucco, Michael L. Betaines and Related Osmoprotectants. Targets for Metabolic Engineering of Stress Resistance. *Plant Physiology* Aug. 1, 1999 vol. 120 no. 4 945-949

Hanson, Andrew D., McNeil, Scott D., Nuccio, Michael L., and Rhodest, David, Metabolic engineering of plants for osmotic stress resistance. *Curr Opin Plant Biol.* 1999 April; 2(2):128-34

Hirai, Nobuhiro, Iwamura, Hajime, Sugizaki, Harujuki, Wakabayashi, Kohji, and Yoshikawa, Masami Succinic and lactic acids as plant growth promoting compounds produced by rhizospheric *Pseudomonas putida* Canadian Journal of Microbiology, 1993, 39(12): 1150-1154, 10.1139/m93-173

Horbowicz, Marcin, Koczkodaj, Danuta, Kosson, Ryszard, Mitrus, Joanna, and Saniewski, Marian. Effects of simultaneous use of methyl jasmonate with other plant hormones on the level of anthocyanins and biogenic amines in seedlings of common buckwheat (*Fagopyrum esculentum* Moench). *ACTA Agrobotanic* Vol. 66 (1), 2013: 17-26 DOI: 10.5586/aa. 2013.003

Hong, Soon-Kwan and Sun, Yan-Lin, Effects of plant growth regulators and 1-glutamic acid on shoot organogenesis in the halophyte *Leymus chinensis* (Trin.). *Plant Cell Tiss Organ Cult* (2010) 100:317-328 DOI 10.1007/s 11240-009-9653-4

Irsfeld, Meredith, Pruess, Dr Birgit, and Spadafore, Matthew, A-phenylethylamine, a small molecule with a large impact. *Webmedcentral.* 2013 Sep. 30; 4(9). pii: 4409.

Kalamaki, Mary S., Kanellis, Angelos K., and Merkouropoulos, Georgios, Can ornithine accumulation modulate abiotic stress tolerance in *Arabidopsis? Plant Signaling & Behavior* 4:11, 1099-1101; November 2009; © 2009 Landes Bioscience Kanzaki, Hiroshi, Kawazu, Kazuyoshi, Kobayashi, Akio, Mikawa, Takashi, Murakami, Tadashi, 30 Ono, Youko, and Yoshikawa, Nobuji. Isolation and Characterization of Two Novel Nematicidal Depsipeptides from an Imperfect Fungus, Strain D1084. *Bioscience, Biotechnology and Biochemistry* ISSN:0916-8451 (Print) 1347-6947

Kopcke B., Schwartz, M., Sterner O, and Weber R. W., Anke H. 3-hydroxypropionic acid as a nematicidal principal in endophytic fungi. *Photochemistry* Vol. 65, Issue 15, August 2004, Pages 2239-2245

Kramera, Karl J. and Muthukrishnanb, Subbaratnam. Insect Chitinases: Molecular Biology and Potential Use as Biopesticides. *Insect Biochem Mol* Biol. 1997 November; 27(11):887-900

Lee, W J. Role of Oxoproline in the Regulation of Neutral Amino Acid Transport across the Blood-Brain Barrier. *J Biol Chem.* 1996 Aug. 9; 271(32):19129-33

Liu, Dong, Liu, Yule, Wang, Guodong, Yu, Hailan, and Zhang, Fengxia, Partial deficiency of isoleucine impairs root development and alters transcript levels of the genes involved in branched-chain amino acid and glucosinolate metabolism in *Arabidopsis. J. Exp. Bot.* (2012)

Lu, Q., Peng, Z., and Verma, D. P. S., Reciprocal regulation of Δ 1-pyrroline-5-carboxylate synthetase and proline dehydrogenase genes controls proline levels during and after osmotic stress in plants. *Mol. Gen Genet.* 1996 Dec. 13; 253(3):334-41.

Luis A., Corpas, F. Javier, McCarthy, Iva, Palma, Jose M., Romero-Puertas, Maria C., and Sandalio, Luisa M., Plant proteases, protein degradation, and oxidative stress: role of peroxisomes del Rio. Plant Physiology and Biochemistry Volume 40, Issues 6-8, June-August 2002, Pages 521-530

Mizuno, T., Yamashino, T. Biochemical characterization of plant hormone cytokinin-receptor histidine kinases using microorganisms. *Methods Enzymol.* 2010; 471:335-56. doi: 10.1016/S0076-6879(10)71018-1. Epub 2010 Mar. 1

Murata, N. and Sakamoto, A. The role of glycine betaine in the protection of plants from stress: clues from transgenic plants. *Plant Cell Environ.* 2002 February; 25(2):163-171.

Nakayama, F. S. Guayule future development. 200S. Industrial Crops and Products, Volume 22, Issue 1, July 200S, Pages 3-13.

Oliveira, D. F.; Campos, V. A. C.; Machado, A. R. T.; Silva, W. R. J.; Zeri, A. C. M.; Campos, V. P. Influence of volatile organic substances on the reproduction of *Meloidogyne incognita* in soybean and cotton plants. *Nematologia Brasileira* 2011 Vol. 35 No. ¾ pp. 55-62

Oliver, Melvin J and Wood, Andrew J. Translational control in plant stress: the formation of messenger ribonucleoprotein particles (mRNPs) in response to desiccation of *Tortula ruralis* gametophytes. *The Plant Journal* Volume 18, issue 4 May 1999 pages 359-370

Succinic Acid 2,2-Dimethylhydrazide Succinic acid is a dwarfing agent that can affect fruit-bud initiation, 2,2-Dimethylhydazide, Daminozide. *Phytotechnology Laboratories* print email S746

Urao, T., Yamaguchi-Shinozaki, K. Plant histidine kinases: an emerging picture of two-component signal transduction in hormone and environmental responses. *Sci STKE.* 2001 Nov. 20; 2001(109):re18.

What is claimed is:

1. A method for inducing bud and/or flower formation in a plant wherein said method comprises contacting the plant, or its environment, with a composition comprising a bioactive aqueous extract from the roots of a *Parthenium argentatum* Gray plant wherein said roots have been separated from the rest of the plant, milled to a size of ¼ inch or less, and extracted by placing them in an aqueous solvent; and wherein the milled roots have been removed from the aqueous solvent thereby obtaining the bioactive aqueous extract, and wherein the composition comprises at least 15 compounds selected from ornithine; butane-2,3-diol; alanine; erythritol; mannitol; lyxitol; valine; quinic acid; 3-hydroxypropionic acid; phenylethylamine; succinic acid; 6-deoxyglucose; glycine; myo-inositol; lactic acid; glutamic acid; aspartic acid; putrescine; isoleucine; propane-1,3-diol; tyrosine; oxoproline; histidine; phosphate; 3,4-dihydroxycinnamic acid; N-methylalanine; uridine; ribonic acid; glycerol and urea.

2. A method for improving the marketable yield of a plant wherein said method comprises administering to said plant, or the environment of said plant, a composition comprising a bioactive aqueous extract from the roots of a *Parthenium argentatum* Gray plant wherein said roots have been separated from the rest of the plant, milled to a size of ¼ inch or less, and extracted by placing them in an aqueous solvent; and wherein the milled roots have been removed from the aqueous solvent thereby obtaining the bioactive aqueous extract, and wherein the composition comprises at least 15 compounds selected from ornithine; butane-2,3-diol; alanine; erythritol; mannitol; lyxitol; valine; quinic acid; 3-hydroxypropionic acid; phenylethylamine; succinic acid; 6-deoxyglucose; glycine; myo-inositol; lactic acid; glutamic acid; aspartic acid; putrescine; isoleucine; propane-1,3-diol; tyrosine; oxoproline; histidine; phosphate; 3,4-dihydroxycinnamic acid; N-methylalanine; uridine; ribonic acid; glycerol and urea.

3. The method, according to claim 2, wherein the target plant is selected from row crops, field crops, tree crops, citrus crops, fruit crops, turf crops, ornamental crops, vegetables and vine crops.

4. The method, according to claim 2, wherein the composition is applied to both the roots of the plant and to the foliage of the plant.

5. The method, according to claim 2, wherein the composition comprises butane-2,3-diol; erythritol; valine; quinic acid; 3-hydroxypropionic acid; glycine; lactic acid; glutamic acid; aspartic acid and 3,4-dihydroxycinnamic acid.

6. The method, according to claim 1, wherein the target plant is selected from row crops, field crops, tree crops, citrus crops, fruit crops, turf crops, ornamental crops, vegetables and vine crops.

7. The method, according to claim 1, wherein the composition is applied to both the roots of the plant and to the foliage of the plant.

8. The method, according to claim 1, wherein the composition comprises butane-2,3-diol; erythritol; valine; quinic acid; 3-hydroxypropionic acid; glycine; lactic acid; glutamic acid; aspartic acid and 3,4-dihydroxycinnamic acid.

* * * * *

UNITED STATES PATENT AND TRADEMARK OFFICE
CERTIFICATE OF CORRECTION

PATENT NO. : 12,016,283 B2  
APPLICATION NO. : 17/375363  
DATED : June 25, 2024  
INVENTOR(S) : Lance William Beem, Stephen Michael Butler and George Benjamin Cloud Page 1 of 1

It is certified that error appears in the above-identified patent and that said Letters Patent is hereby corrected as shown below:

In the Specification

Column 14,
Line 18, "through a ⅛ inch," should read --through a 1/4 inch,--.

Column 20,
Line 17, "246.6 AB" should read --246.67 AB--.

Signed and Sealed this  
Twenty-fourth Day of September, 2024

Katherine Kelly Vidal  
*Director of the United States Patent and Trademark Office*